(12) United States Patent
Bush et al.

(10) Patent No.: US 10,811,129 B2
(45) Date of Patent: Oct. 20, 2020

(54) CUSTOMIZING NAMES OF INSULIN DELIVERY PROFILES FOR IMPROVED PATIENT SAFETY

(71) Applicant: Roche Diagnostics Operations, Inc., Indianapolis, IN (US)

(72) Inventors: Jason M. Bush, Fishers, IN (US); Christopher R. Halvorson, Carmel, IN (US); Troy L. King, Pendleton, IN (US); James R. Long, Fishers, IN (US); David B. Markisohn, Indianapolis, IN (US); Leon R. Organ, III, Indianapolis, IN (US); Adam R. Scroggin, Noblesville, IN (US); Kaitlin R. Stinson, Indianapolis, IN (US); Kristin M. Westerfield, Indianapolis, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 53 days.

(21) Appl. No.: 13/792,995

(22) Filed: Mar. 11, 2013

(65) Prior Publication Data
US 2014/0257251 A1 Sep. 11, 2014

(51) Int. Cl.
*G16H 20/17* (2018.01)
*G06F 19/00* (2018.01)
*G16H 10/60* (2018.01)
*A61M 5/168* (2006.01)

(52) U.S. Cl.
CPC ......... *G16H 20/17* (2018.01); *G06F 19/3468* (2013.01); *G16H 10/60* (2018.01); *A61M 5/16804* (2013.01); *A61M 2205/502* (2013.01); *A61M 2205/6009* (2013.01)

(58) Field of Classification Search
CPC .... G16H 20/17; G16H 10/60; G06F 19/3468; A61M 2205/502; A61M 2205/6009; A61M 5/16804
See application file for complete search history.

(56) References Cited

U.S. PATENT DOCUMENTS

| | | | |
|---|---|---|---|
| 8,237,715 B2 | 8/2012 | Buck et al. | |
| 2010/0064236 A1* | 3/2010 | Buck et al. | ................... 715/764 |
| 2010/0064243 A1 | 3/2010 | Buck et al. | |
| 2010/0064257 A1 | 3/2010 | Buck et al. | |
| 2010/0077198 A1 | 3/2010 | Buck et al. | |
| 2011/0144586 A1* | 6/2011 | Michaud et al. | ............. 604/151 |
| 2011/0154237 A1 | 6/2011 | Bush et al. | |

* cited by examiner

Primary Examiner — Christopher L Gilligan
(74) Attorney, Agent, or Firm — Harness Dickey

(57) ABSTRACT

Configuration software implements techniques for customizing names of insulin delivery profiles with improved patient safety. The techniques include: receiving a string of characters which serve as a name for a given insulin delivery profile, where the insulin delivery profile includes at least one parameter pertaining to insulin delivery by an insulin pump and is one of a plurality of insulin delivery profiles associated with a given patient; normalizing the string of characters in accordance with a rule set; comparing the normalized string of characters with names for each of the plurality of insulin delivery profiles; and updating the name of the given insulin delivery profile in a pump configuration file residing on the configuration device when the normalized string of characters is unique in relation to the names of the plurality of insulin delivery profiles.

12 Claims, 29 Drawing Sheets

CUSTOMIZING NAMES OF INSULIN DELIVERY PROFILES FOR IMPROVED PATIENT SAFETY

FIELD

The present disclosure relates generally to pump configuration software and, more particularly, to customizing names of insulin delivery profiles using the pump configuration software.

BACKGROUND

An insulin pump is a fluid infusion device for delivering insulin to people who suffer from diabetes. The pump, which is worn by the user and eliminates the need for multiple daily insulin injections, closely imitates a normally functioning pancreas by releasing hundreds of small doses of insulin each day into the body through an infusion set to regulate blood glucose levels. The rate of delivery of these small doses (i.e., the basal rate) varies from user to user. Indeed, even for a particular user, the basal rate varies throughout the day, and depends upon a variety of factors such as the user's internal clock, metabolism, physical health, and level of stress and exercise.

As the amount and rate of insulin delivery (both basal and bolus) must be tailored to the individual needs of the user, modern pumps are programmable. Some pumps are capable of communicating with a separate computing device, and are compatible with programming software applications that may be executed on the computing device. The programming software permits an operator, such as the user or a health care provider, to customize the settings of the various parameters that affect the pump's operation. These parameters are included in a configuration file that is executed by the pump, and include hourly basal rates, maximum hourly basal rates, bolus dose settings, communication settings, battery settings, and many others. For example, using programming software, a user may upload a configuration file from the user's pump, modify the settings for certain parameters to change the operation of the pump, and save the modified configuration file to the pump. Alternatively, a health care provider responsible for programming the pumps of multiple patients may select an initial generalized configuration file stored in a source location such as a pump or memory location of a computing device as a starting point for programming the patients' pumps. Many of the parameter settings of the initial configuration file (e.g., battery type, language, etc.) may be suitable for all of the pumps to be programmed. Other settings (e.g., hourly basal rates, bolus dose settings, etc.) may be unique to each patient's pump. Moreover, some of these settings may be further customized by the patient. After the health care provider selects the initial configuration file, he or she may change only the settings needed to customize the pump's operation for the current patient, then save the customized configuration file to the patient's pump without having to define a setting for every pump parameter.

A basal rate profile consists of one or more basal rates defined to cover the 24 hours of the day (e.g., 24 hourly basal rates). Many users use different basal rate profiles for different circumstances. For example, one basal rate profile may be used for weekdays, another profile (i.e., with different hourly basal rates) for weekends, and another profile for vacation days. These different basal rate profiles are designed to accommodate the expected differences in the user's background insulin needs resulting from variations in the user's sleep patterns, levels of exercise and stress, health condition, menstrual cycle status, etc. during such periods. Accordingly, users typically use a plurality of different basal rate profiles depending upon their anticipated condition/activities for the day (i.e., weekday, weekend, vacation, illness, etc.). A typical configuration file may include a set of basal rate profiles for selection by the user.

One aspect of the programming software enables the patient or their healthcare provider to customize the names of the basal profiles for ease of use. Because insulin delivery can directly affect the health of the patient, it is important that the programming software incorporate safety measures to prevent operators from inadvertently programming a pump with parameter settings that may harm the user or adversely affect the operation of the pump. As it relates to this feature, it is desirable that the programming software implement measures that ensure profile names are customized safely.

This section provides background information related to the present disclosure which is not necessarily prior art.

SUMMARY

Configuration software implements techniques for customizing names of insulin delivery profiles with improved patient safety. The techniques include: receiving a string of characters which serve as a name for a given insulin delivery profile, where the insulin delivery profile includes at least one parameter pertaining to insulin delivery by an insulin pump and is one of a plurality of insulin delivery profiles associated with a given patient; normalizing the string of characters in accordance with a rule set; comparing the normalized string of characters with names for each of the plurality of insulin delivery profiles; and updating the name of the given insulin delivery profile in a pump configuration file residing on the configuration device when the normalized string of characters is unique in relation to the names of the plurality of insulin delivery profiles. Conversely, the user is prompted to change the name when the normalized string of characters matches a name of one of the plurality of insulin delivery profiles.

In some embodiments, a set of predefined insulin delivery profiles may be stored by the configuration device. The normalized string of names is also compared to each of the default names in the set of predefined insulin delivery profiles.

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
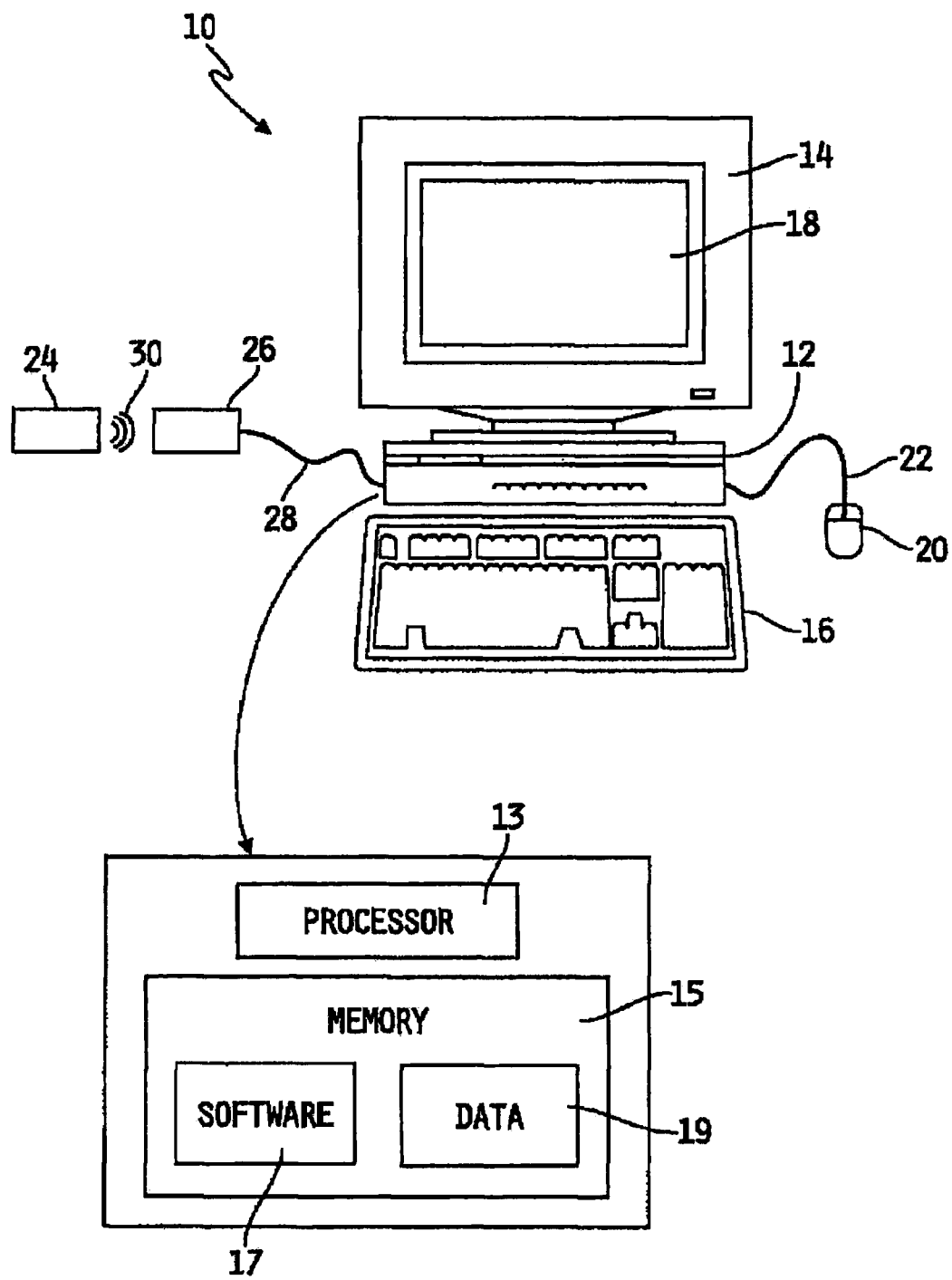
FIG. 1 is a conceptual diagram of a computing device in communication with an insulin pump.

FIG. 1 depicts an exemplary embodiment of an insulin pump configuration system 10, some or all of the components of which may be used in conjunction with the teachings of the present disclosure. System 10 generally includes a computing device 12, shown here in the form of a computer having display device 14, in this case a computer video screen or monitor having screen 18, a keyboard 16, a processor 13, and memory 15, which may contain the configuration software 17 of the present disclosure and data 19 as is further described herein. While described and depicted herein with specific reference to a computer, certain concepts of the present disclosure may be utilized in conjunction with any computing device capable of operating pump programming software. Computing device 12 also has a pointing device or mouse 20 connected to it by cable 22 (or wirelessly). While mouse 20 and keyboard 16 are shown, system 10 may include any input device such as a touchpad, joystick, touch screen, trackball, etc.

Computing device 12 may include a variety of computer-readable media. Computer-readable media can be any available media that can be accessed by computing device 12 and includes both volatile and non-volatile media, and removable and non-removable media. By way of example, and not limitation, computer-readable media may comprise computer storage media and communication media. Storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules and other data and which can be accessed by computing device 12. Computer-readable media may be accessed directly or through a network such as the Internet.

System 10 is configured to provide information to, and receive information from, infusion pump 24. Again, while an infusion pump, and more particularly an insulin pump, is described herein, it should be understood that the teachings of the present disclosure may also apply to devices such as "smart" insulin pens or other such devices known or hereafter developed. In FIG. 1, computing device 12 is shown coupled to communication media or dongle 26, in this case a modulated signal transceiver, accessible to computing device 12 by means of cable 28, and configured to transmit and receive modulated signal 30 to establish logical communication with pump 24. In another exemplary embodiment, computing device 12 and pump 24 may include ports configured to establish a physical connection. By way of example, and not limitation, dongle 26 may include wired media such as a wired network or direct wired connection, and wireless media such as acoustic, RF, infrared and other wireless media. More specifically, dongle 26 as depicted includes an infrared port for communication with a similar infrared port of pump 24.

Figure 2:
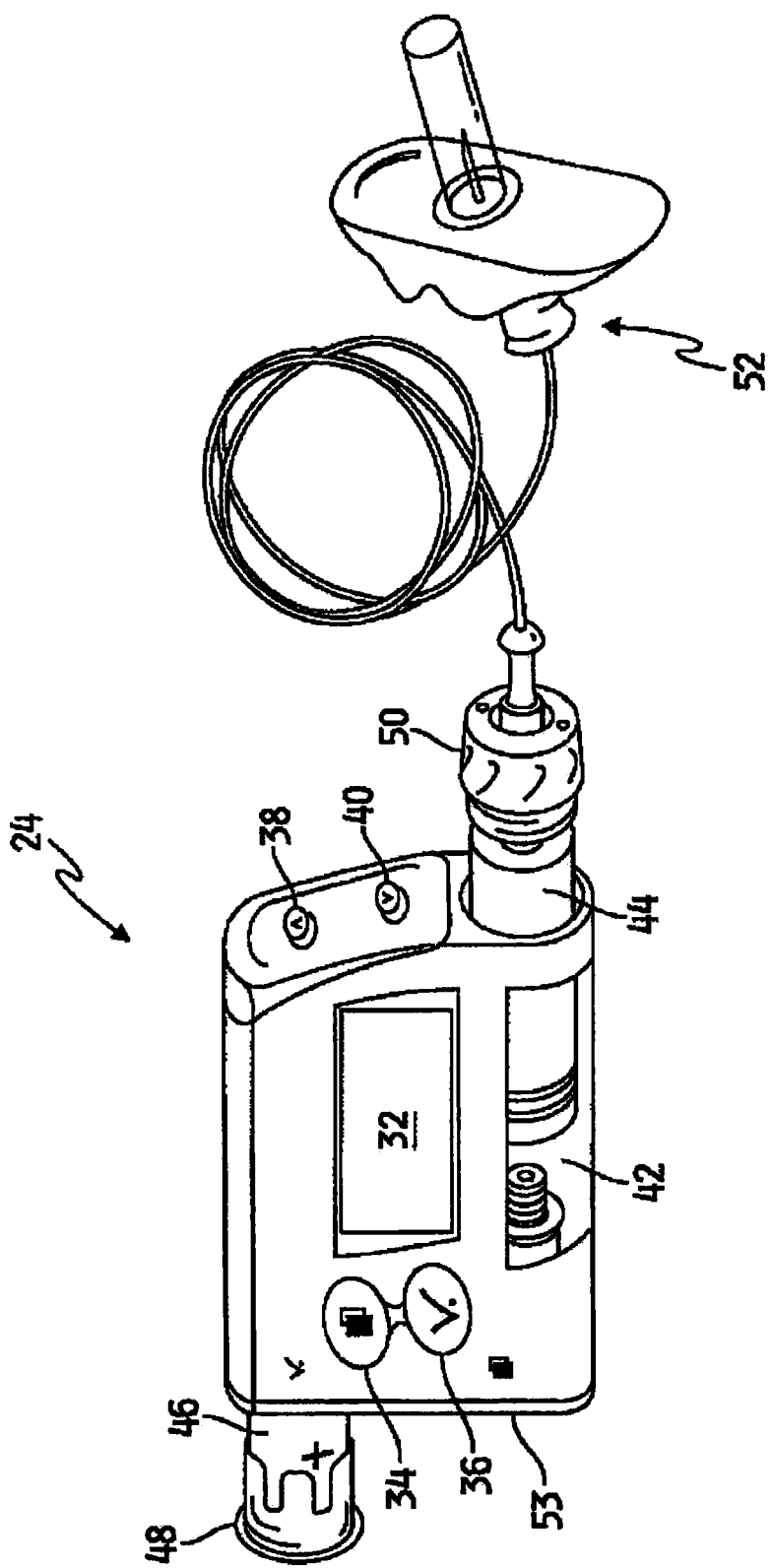
FIG. 2 is perspective view of an insulin pump coupled to an infusion set.

Referring now to FIG. 2, pump 24 includes a display 32 for displaying information to an operator or user, a menu button 34 for navigating though the various functions provided by pump 24, a check button 36 for selecting options, an up key 38 and down key 40 for scrolling through options and controlling certain insulin delivery functions, a cartridge receptacle 42 for storing an insulin cartridge 44, a battery 46 (shown partially inserted), a battery cap 48 (shown unsecured to pump 24), an adapter 50 for physically coupling cartridge 44 to an infusion set 52, and a communication port 53 for sending information to, or receiving information from, computing device 12 through dongle 26.

Figure 3:
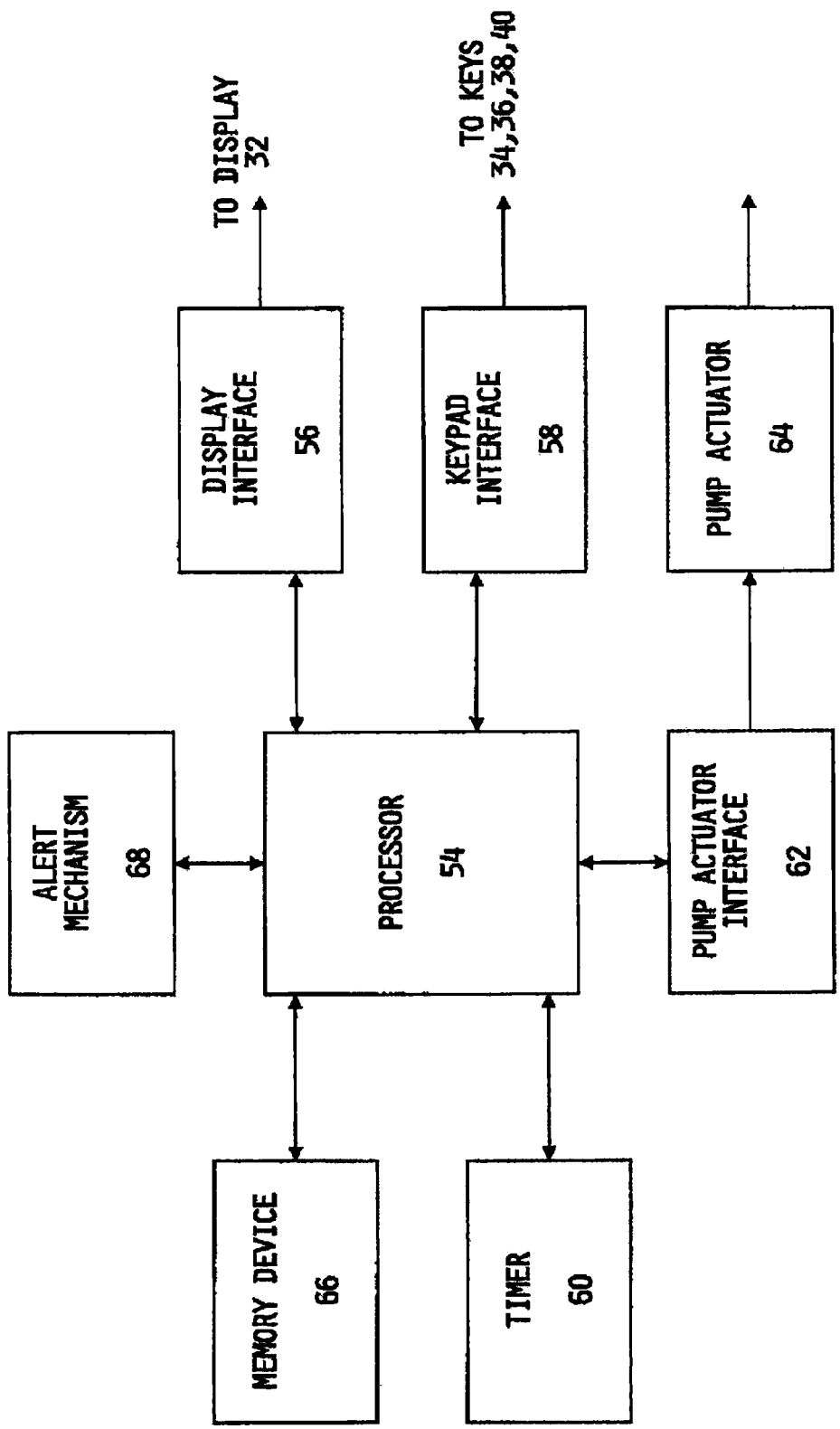
FIG. 3 is a block diagram of internal components of the pump of FIG. 2.

FIG. 3 provides a block diagram representation of internal components of pump 24. As shown, pump 24 includes a processor 54 coupled to a display interface 56, which is coupled to display 32. Processor 54 is also coupled to a keypad interface 58 which is coupled to keys 34, 36, 38, 40, and a pump actuator interface 62 which is coupled to an actuator 64 suitable for delivering insulin doses (medical infusion pumps other than insulin pumps will deliver doses of other medicament). Processor 54 is further coupled to a memory device 66 that stores application programs and data, including the configuration files described herein. It is understood that data described as residing in the configuration file may reside in a single file or be spread across multiple data stores which are referred to collectively as the configuration file. Memory device 66 is constructed of any combination of volatile and/or nonvolatile memory suitable for a particular embodiment. Processor 54 is also coupled to an alert mechanism 68, that, in various embodiments is a buzzer, a vibrator, a light emitting diode, or the like, suitable for providing audible, tactile, or visual alerts to an insulin pump user. Finally, processor 54 is coupled to a timer 60, which is capable of maintaining a current time, including time of day and day of the week.

Figure 4:
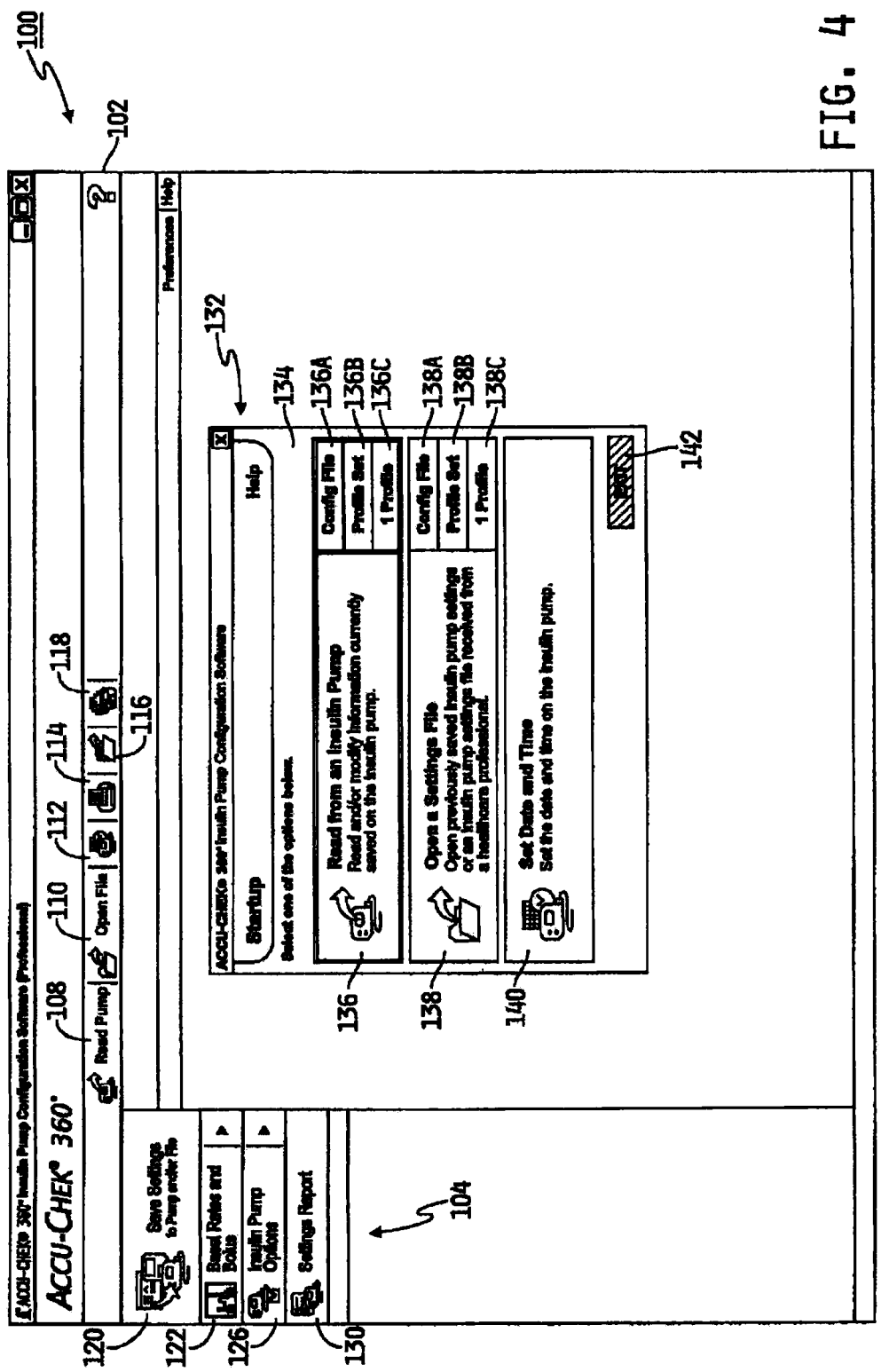
FIG. 4 is a screenshot of a home screen displayed upon activation of software according to teachings of the present disclosure.

FIG. 4 depicts the home screen 100 displayed upon activation of software 17. Home screen 100 generally includes a toolbar 102, a navigation menu 104, and an active window 106. Toolbar 102 includes a read pump icon 108, an open file icon 110, a date/time icon 112, a print icon 114, a load all profiles from file icon 116, and a save all profiles to a file icon 118. Navigation menu 104 includes a save settings button 120, a basal rates and bolus button 122, an insulin pump options button 126, and a settings report button 130. The content of active window 106 changes depending upon the operation being performed by software 17. Here, active window 106 includes a start up dialog box 132.

Start up dialog box 132 includes a message area 134, a read pump area 136 with a configuration file button 136A, a profile set button 136B, and a single profile button 136C, an open area 138 with a configuration file button 138A, a profile set button 138B, and a single profile button 138C, a set date/time button 140, and an exit button 142. For the purpose of this description, the operator will be described as obtaining an insulin pump configuration file 141 from memory 15 (i.e., where it is stored as data 19) of computing device 12 using open configuration file button 138A. It should be understood that the options for retrieving a configuration file, a profile set or a single profile provided by buttons 138A, 138B, and 138C, respectively, are also accessible by activating open file icon 110 on toolbar 102.

As is further described herein, the processes for saving information to pump 24 or to memory 15 on computing device 12 differs. The process for obtaining or retrieving such information from either pump 24 or memory 15 on computing device 12, however, is not meaningfully different for the purpose of the present disclosure. Accordingly, it is sufficient to note that the functions of read pump configuration file button 136A, read pump profile set button 136B, and read pump single profile button 136C (all of which are also accessible by activating read pump icon 108 on toolbar 102) are not expressly described herein except to say that they are similar to the functions of buttons 138A, 138B, and 138C. The operator begins the process of opening configuration file 141 stored in memory 15 by activating open configuration file button 138A.

Figure 5:
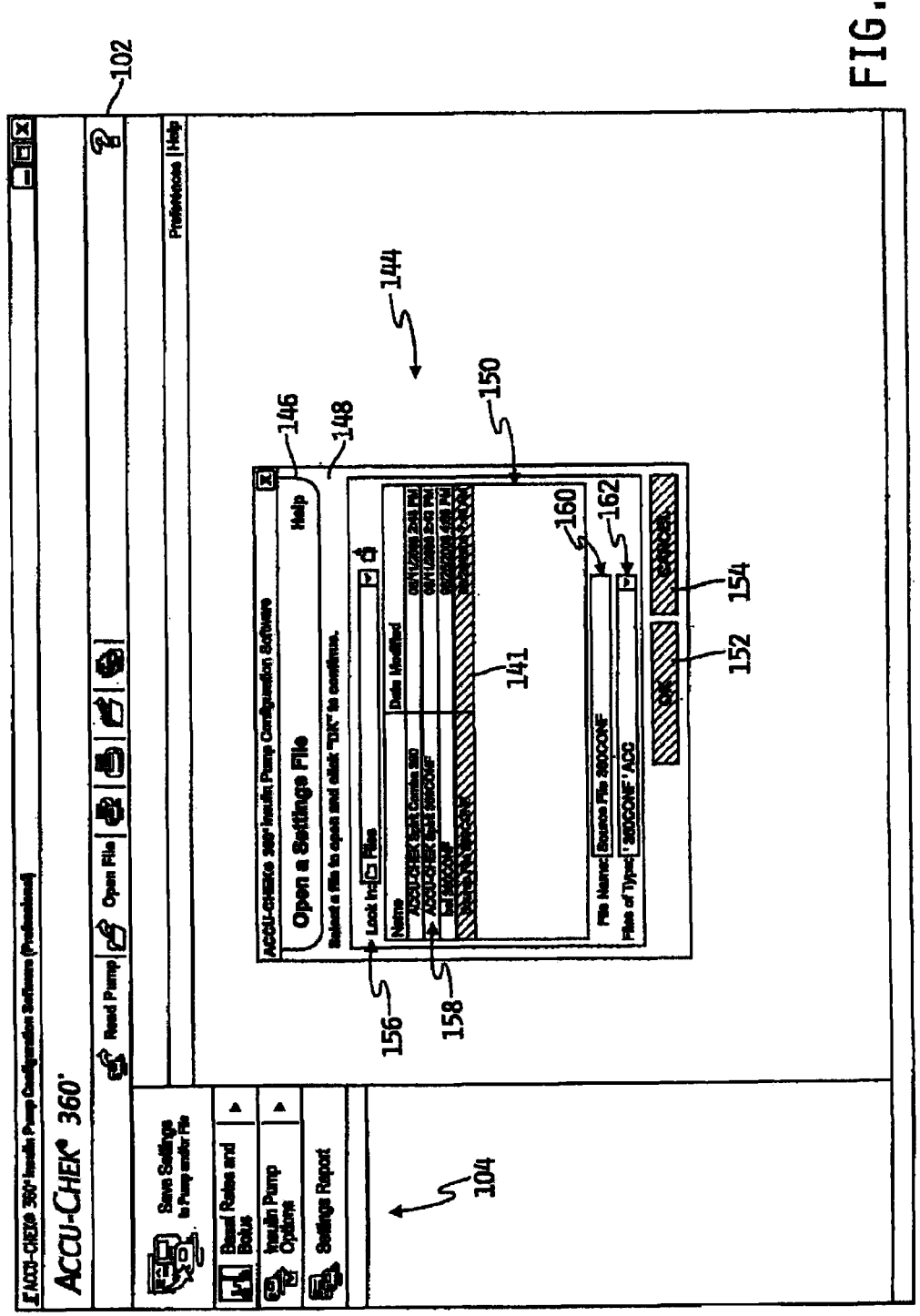
FIG. 5 is a screenshot including an open file dialog box.

As is shown in FIG. 5, when the operator activates open configuration file button 138A, start up dialog box 132 in active window 106 is replaced by open settings file dialog box 144. Open settings dialog box 144 includes a title bar 146 which describes the operation being performed, a message area 148 which provides instructions to the operator for performing the operation, a file selection window 150, an OK button 152 and a cancel button 154. File selection window 150 includes a file location area 156 for defining a folder location of files using a conventional tree structure, a file information area 158 that provides information about the files in the folder selected using file location area 156, a file name area 160 that includes the name of a file selected from file information area 158, and a file type area 162 for limiting, in a conventional manner, the types of files in the currently selected folder to be displayed in the file information area 158. Here, the operator highlights the source file named Source File.360CONF and activates OK button 152 to retrieve configuration file 141.

Figure 6:
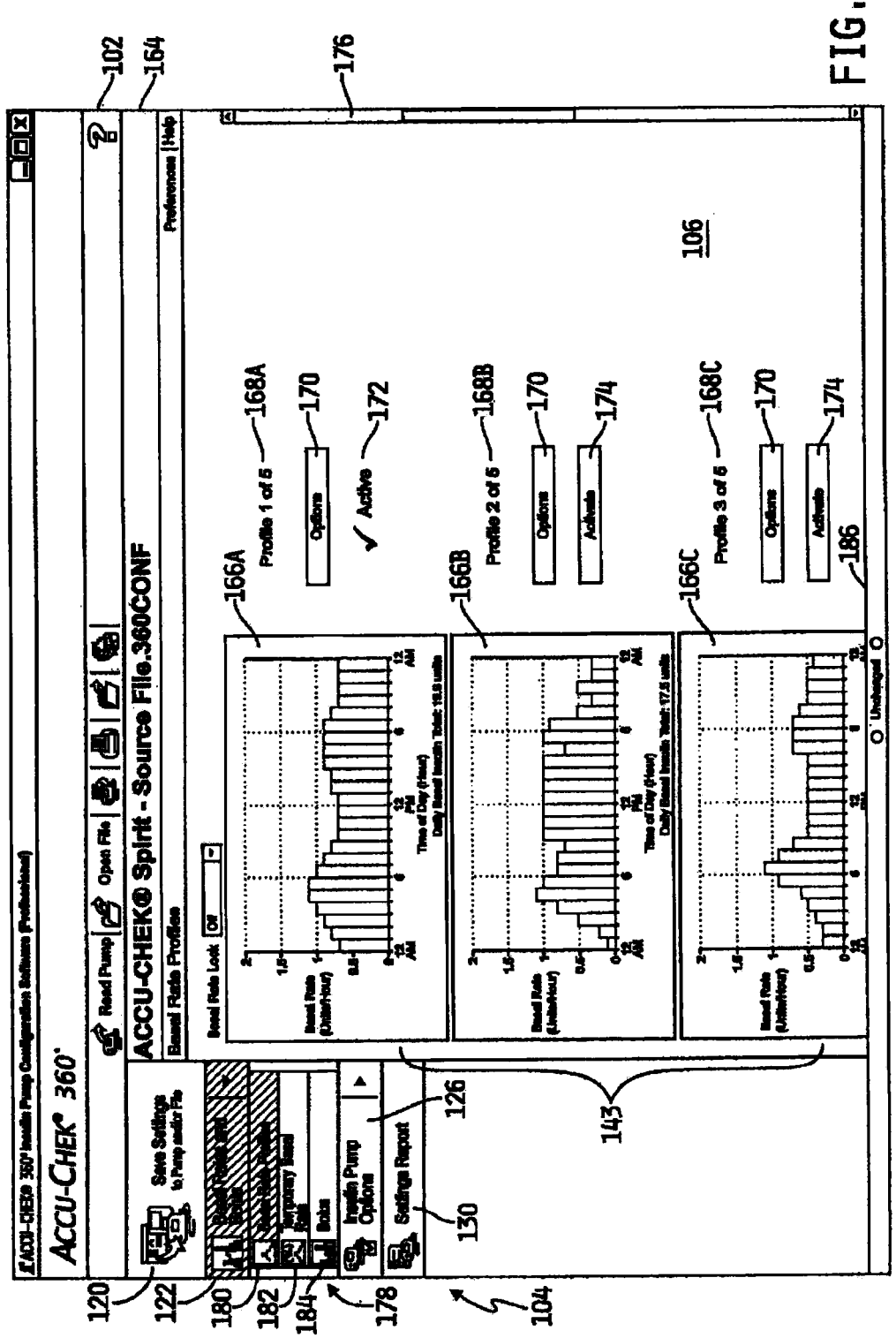
FIG. 6 is a screenshot generated upon activating a configuration file.

After configuration file 141 is retrieved from memory 15 of computing device 12, the operator is provided information in active window 106 regarding the basal rate profiles included in configuration file 141 as depicted in FIG. 6. In the depicted context, active window 106 includes a title bar 164 that identifies the active file (or if the active file is uploaded from pump 24, the pump name and serial number), at least one thumbnail image 166A-C that functions as a graphic preview of the data associated with a basal rate profile included in configuration file 141, at least one profile indicator 168A-C indicating the number of the corresponding basal rate profile represented by the associated thumbnail image 166A-C, at least one options button 170, and an active icon 172 and/or an activate button 174. In one embodiment of the present disclosure, configuration file 141 includes a basal rate profile set 143 consisting of five individual basal rate profiles. Accordingly, as depicted in the figure, a thumbnail image 166A-C, profile indicator 168A-C, options button 170, and an active icon 172 and/or an activate button 174 is displayed for each profile in profile set 143. In the description that follows, only the first three of the five possible basal rate profiles are used. The operator may view basal rate profile information not shown in active window 106 by using scroll bar 176.

By default, the first depicted profile is designated as active by software 17. As such, active icon 172 is shown in association with thumbnail image 166A instead of activate button 174. The operator may select other available profiles to be made active by selecting the activate button 174 associated with the desired profile. As is also shown in FIG. 6, when a configuration file is opened or uploaded and active window 106 is populated with basal rate profile information, basal rate and bolus button 122 is automatically activated, causing the display of dropdown menu 178 in navigation menu 104. Dropdown menu 178 is also displayed upon opening or uploading a profile set or individual profile. Dropdown menu 178 includes a basal rate profile button 180 (which is depicted as active), a temporary basal rate button 182, and a bolus button 184. Finally, active window 106 further includes a status bar 186 which indicates the status of the currently active configuration file 141. Here, the status is unchanged.

The basal rate profiles associated with thumbnail images 166A-C may be modified in the manner described in co-pending U.S. patent application Ser. No. 12/205,582 entitled "METHOD AND SYSTEM FOR MANIPULATING GROUPS OF DATA REPRESENTATIONS OF A GRAPHICAL DISPLAY", and U.S. patent application Ser. No. 12/205,587 entitled "INSULIN PUMP CONFIGURATION PROGRAMMING INVALID SETTINGS NOTIFICATION AND CORRECTION", the entire contents of which are hereby expressly incorporated herein by reference. Also, it should be understood that although portions of this description refer to hourly basal rate profiles, basal rate profiles may include basal rates that cover more or less than a one hour time period. Indeed, the time periods covered by basal rates in a profile need not be equal. The concepts of the present disclosure are not limited by the duration of an individual basal rate, and the references to hourly basal rates are only exemplary.

Figure 7:
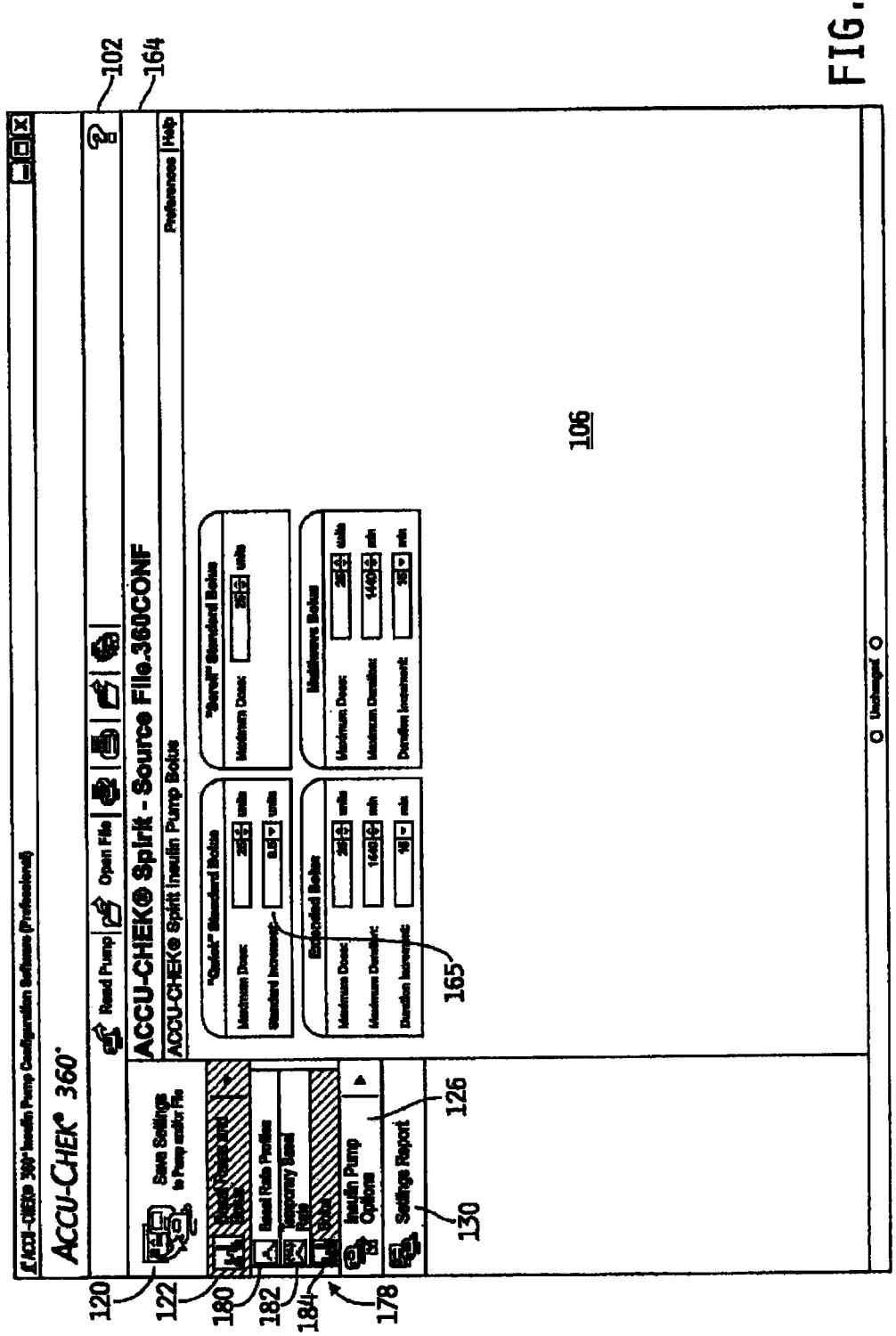
FIG. 7 is a screenshot depicting settings for bolus parameters.

As indicated above, configuration files include information other than basal rate profiles. For example, by activating bolus button 184, the operator has access to various bolus dose settings as shown in FIG. 7, all of which are known to persons skilled in the art. For purposes of the present description, it should be noted that the standard increment for "Quick" Standard Bolus 165 is set to 0.5. This is the amount of bolus insulin to be included in a bolus injection to compensate for carbohydrate consumption each time the user depresses up key 38. This bolus increment is an important pump parameter because inappropriately large bolus injections may cause the user to lose consciousness, which can be life threatening under a variety of circumstances (such as driving).

Figure 8:
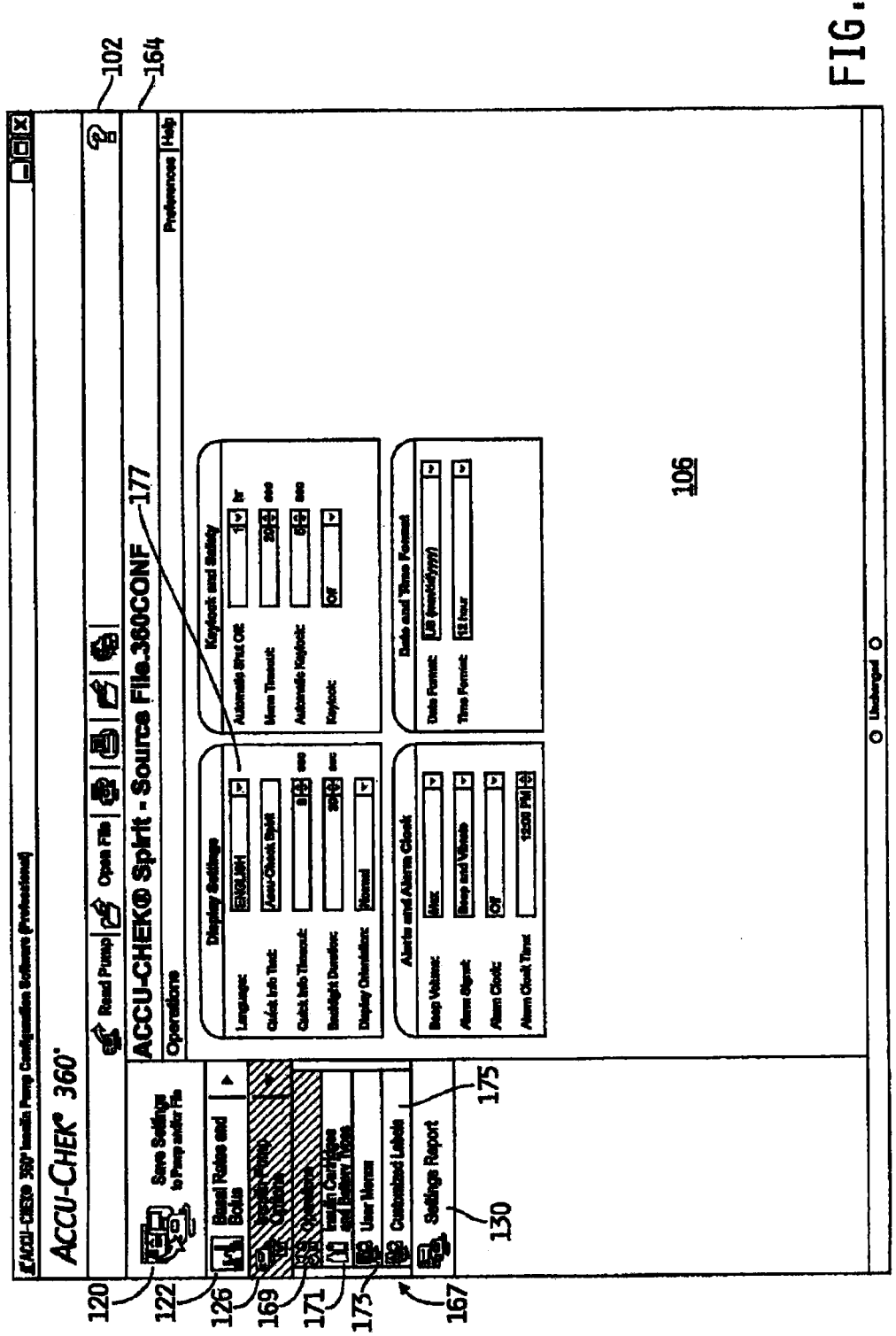
FIG. 8 is a screenshot depicting settings for various pump operations.

FIG. 8 depicts the various parameter settings accessible by activating insulin pump options button 126, which causes the display of dropdown menu 167, including operations button 169, cartridges and battery button 171, user menus button 173, and customized labels button 175. Activation of any of buttons 169, 171, 173, and 175 provide parameter settings options in active window 106. FIG. 8 depicts the parameter options displayed upon activation of operations button 169. For purposes of the present description, it should be noted that the language option 177 is set to English.

Figure 9:
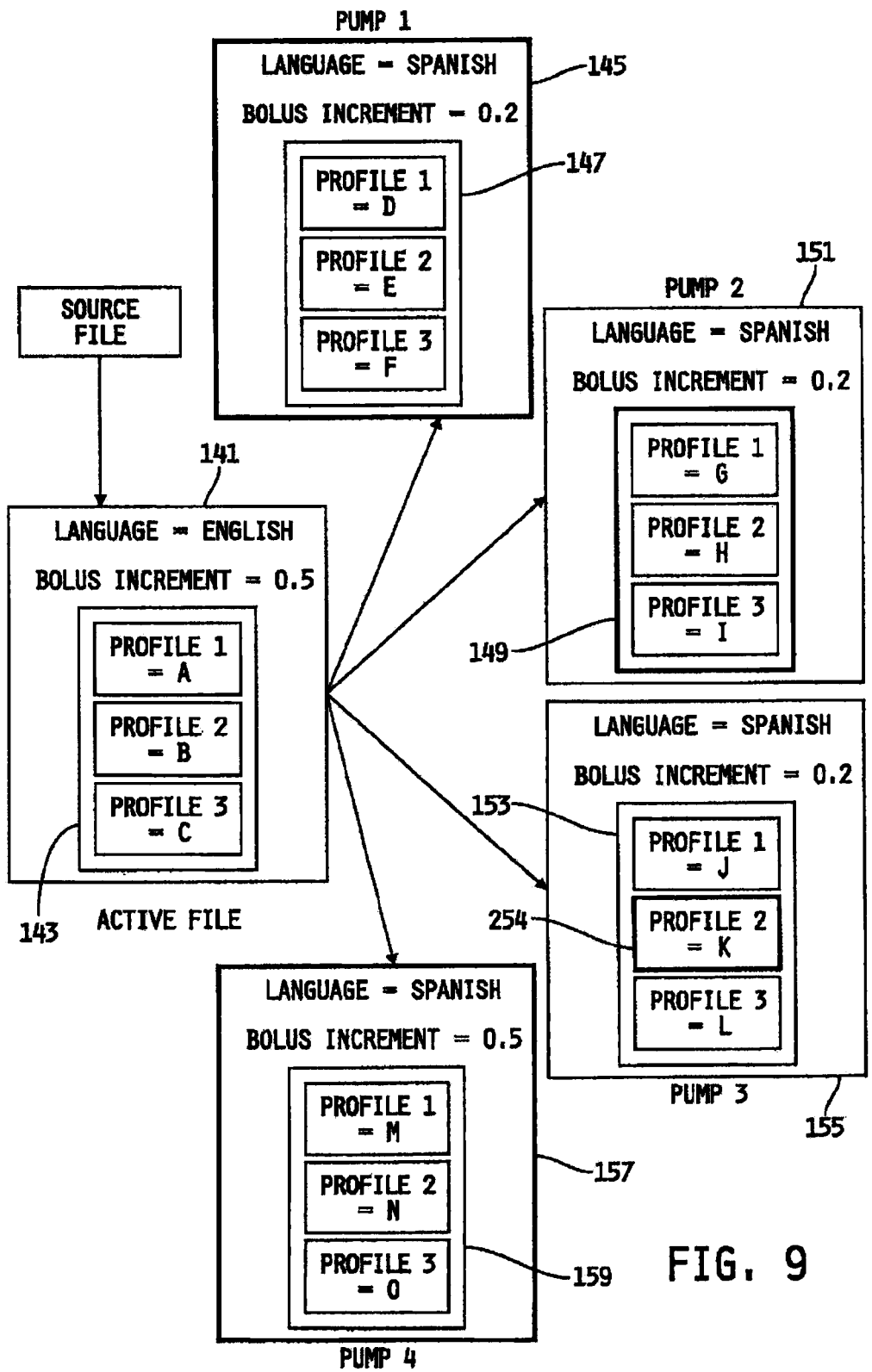
FIG. 9 is a conceptual diagram of various pump programming operations using an active configuration file.

At this point in the illustrative example, an entire configuration file 141 (i.e., Source File.360CONF) has been loaded by software 17 as the active file. To illustrate the principles of the present disclosure, assume that an operator (such as a health care provider) has loaded configuration file 141 for the purpose of programming four separate insulin pumps. FIG. 9 is a conceptual drawing illustrating the programming operations described in the remainder of this description. Configuration file 141 is depicted as the active file, obtained from a source file in the manner described above. Configuration file 141 includes, among other things, settings for language and bolus increment, as well as profile set 143, including individual basal rate profiles A-C (corresponding to thumbnail images 166A-C of FIG. 6). The language is English and the bolus increment is 0.5. Configuration file 141 will first be described as replacing configuration file 145 currently residing on pump 1, which includes a language parameter setting of Spanish, a bolus increment setting of 0.2, and a profile set 147 including three individual profiles D-F with hourly basal rates that differ from the hourly basal rates of profiles A-C of configuration file 141. Next, profile set 143 of configuration file 141 will be described as replacing profile set 149 of configuration file 151 currently residing on pump 2. Then, individual profile 2 of configuration file 141 will be described as replacing profile 2 of profile set 153 of configuration file 155 currently loaded on pump 3. Finally, to illustrate one kind of oversight the operator may make when replacing an entire configuration file instead of just a profile set or a single profile, configuration file 141 will be described as replacing configuration file 157 (instead of just profile set 159) currently residing on pump 4.

Figure 10:
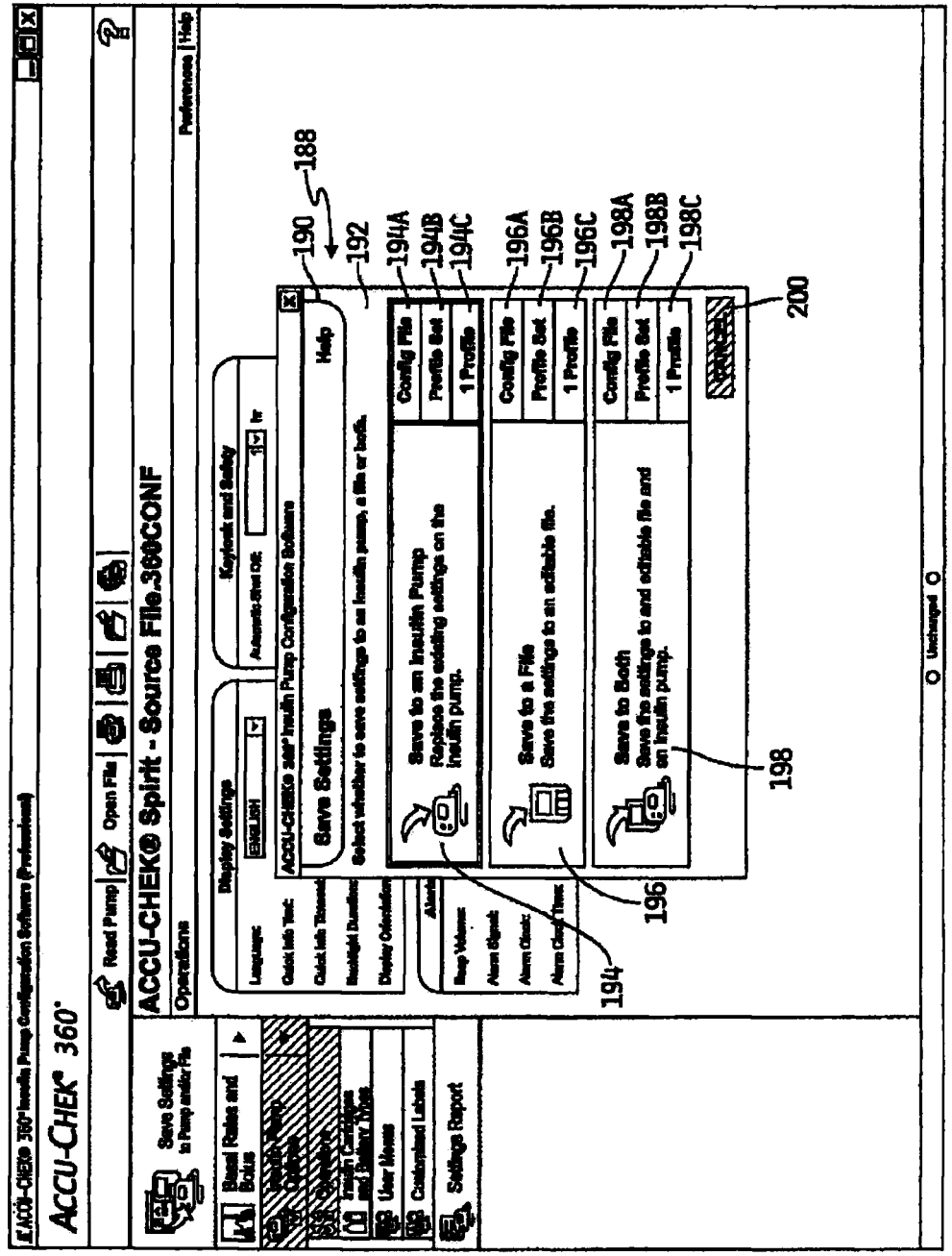
FIG. 10 is a screenshot including a save settings dialog box.

Referring back to FIG. 8, when the operator activates save settings button 120 as the first step in replacing configuration file 145 currently residing on pump 1 with active configuration file 141, the operator is presented with the screen of FIG. 10 which includes pop-up save settings dialog box 188. Dialog box 188 includes a title bar 190, a message area 192, a save to pump area 194 with a configuration file button 194A, a profile set button 194B, and a single profile button 194C, a save to file area 196 including a configuration file button 196A, a profile set button 196B, and a single profile button 196C, a save to both area 198 including a configuration file button 198A, a profile set button 198B, and a single profile button 198C, and a cancel button 200. To replace configuration file 145 with active configuration file 141, the operator activates save to pump configuration file button 194A. Although not depicted in the figures, it should be understood that any of the save to pump functions described herein may be readily adapted to guide the operator through steps for saving information to multiple insulin pumps in a single workflow.

Figure 11:
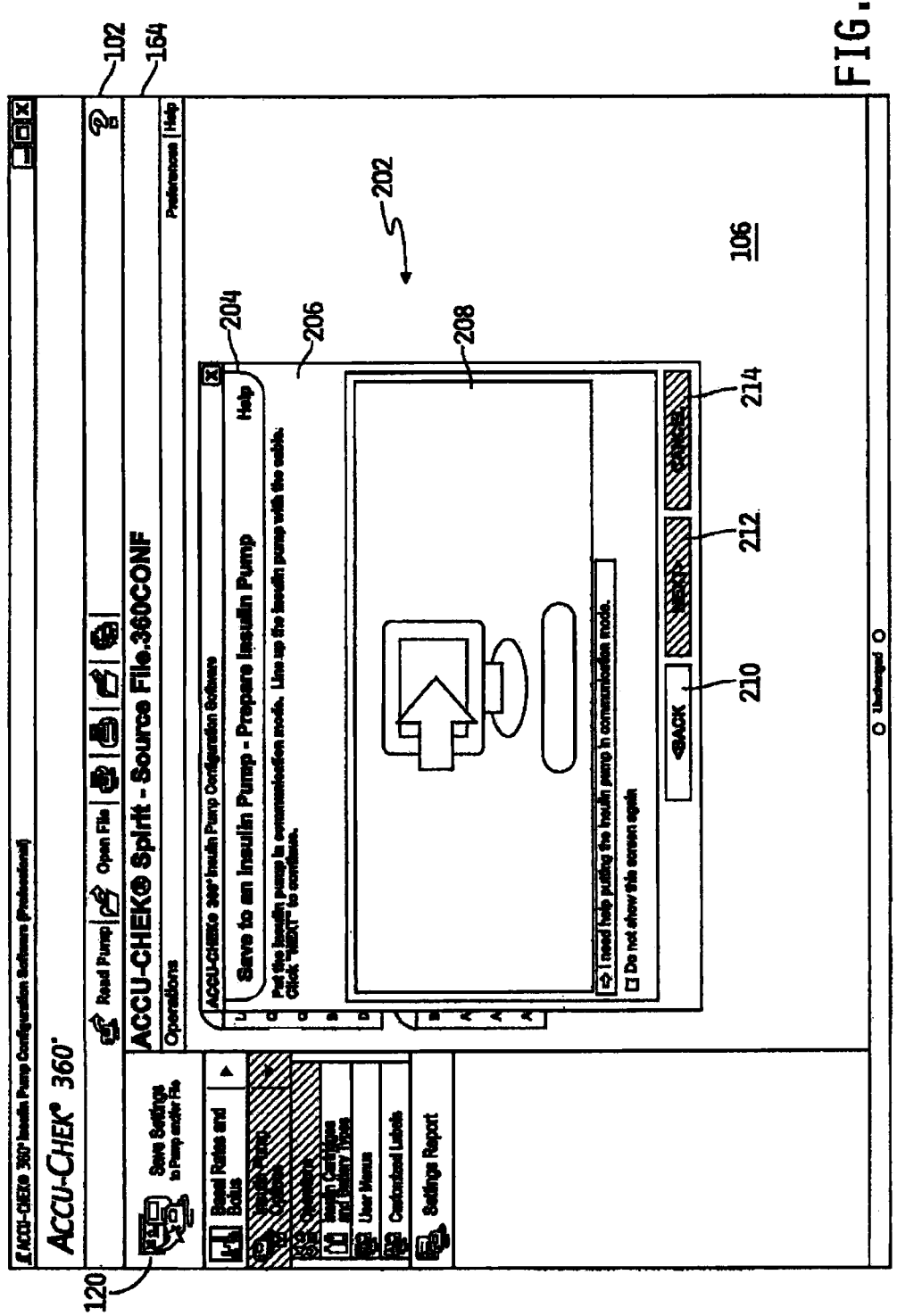
FIG. 11 is a screenshot including a communication status dialog box.

When button 194A is activated, FIG. 11 is displayed, including communication status dialog box 202. Dialog box 202 includes title bar 204, message area 206, status window 208, back button 210, next button 212, and cancel button 214. Title bar 204 indicates that a save to pump operation is being performed. Message area 206 provides instructions to the operator for performing the operation, and status window 208 provides graphical and/or textual information about the operation. As shown in the figure, the operator is provided instructions in message area 206 for preparing pump 1 for communications with computing device 12. A variety of different communication technologies may be employed to facilitate this communication. In this example, the operator is instructed to place pump 1 in communication mode and align pump 1 with dongle 26 for IR communications with computing device 12. When pump 1 is prepared for communications, the operator activates next button 212.

Figure 12:
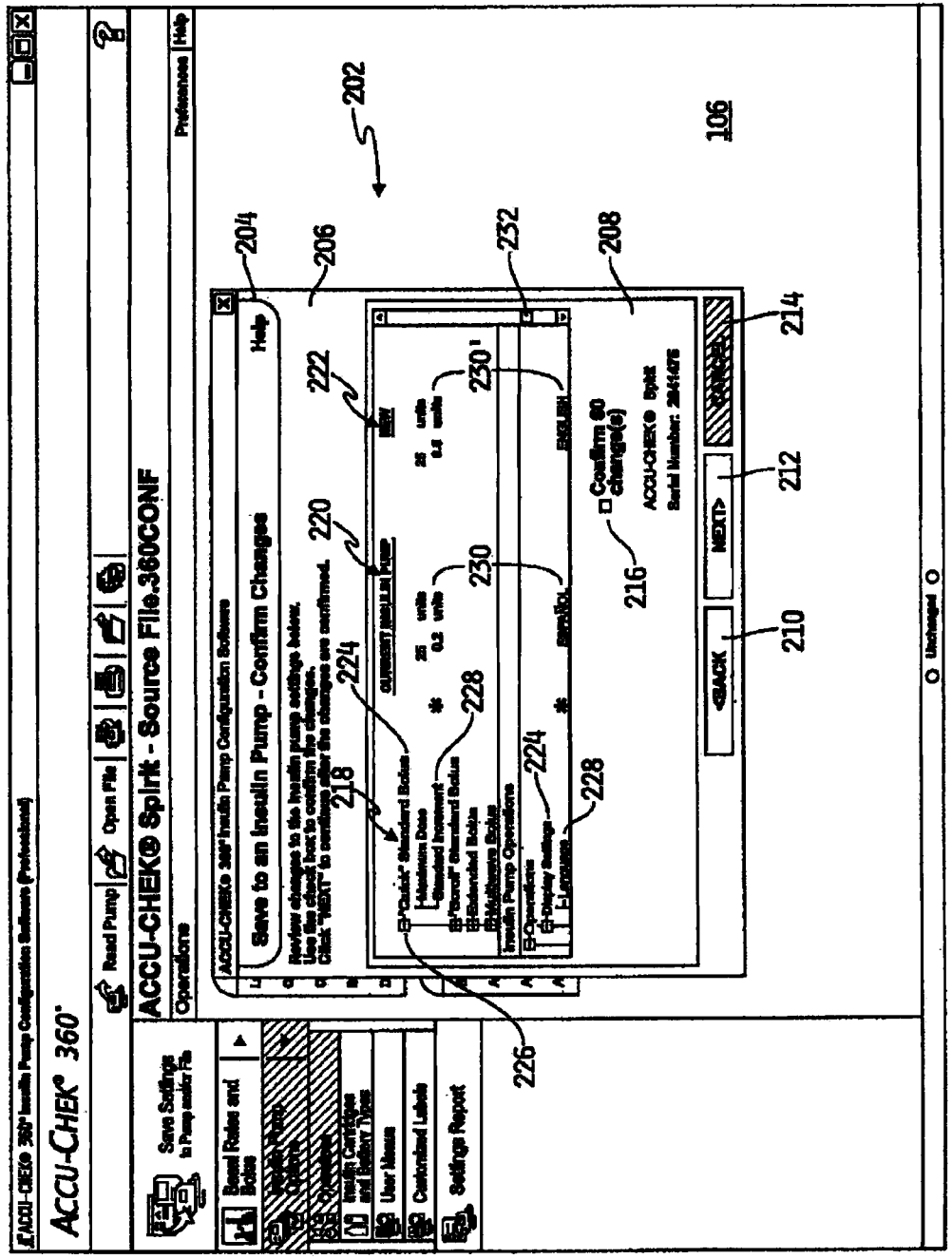
FIGS. 12 and 13 are screenshots wherein the communication status dialog box of FIG. 11 includes a comparison of information to be programmed and a confirm change box.

Before downloading configuration file 141 to pump 1, software 17 displays confirmation instructions in communications status dialog box 202 as depicted in FIG. 11. As shown, message area 206 instructs the operator to review the changes that are about to be made to the pump being programmed, and to check the confirm changes box 216 to approve the changes. Status window 208 includes a configuration file tree structure 218, a current pump information column 220, and a new information column 222. Configuration file tree structure 218 includes a plurality of different parameter titles 224 accompanied by expander icons 226 that, when activated, cause the display of parameter names 228 associated with the parameter title 224. Current pump information column 220 includes data fields 230 corresponding to each displayed parameter name 228. Data fields 230 include the status or value of the named parameter as they exist in the pump about to be programmed (here, pump 1). New information column 222 similarly includes data fields 230' that reflect the data in the active configuration file 141 about to replace the existing configuration file 145 of pump 1. As also shown in FIG. 12, parameters that will change upon programming pump 1 are highlighted. The operator can scroll through the information presented in status window 208 using scrollbar 232.

Although not apparent from FIG. 12, software 17 is configured to automatically position the information in status window 208 such that the most critical information changes may be viewed without having to use scrollbar 232. When more information changes are present than can be simultaneously displayed in the viewable area of status window 208, software 17 is configured to prioritize the changes and automatically position the information such that the most critical information (i.e., changes to parameters most likely to affect the safe operation of pump 24 or the health of the user) is shown in the viewable area of status window 208. Here, the change in bolus increment is shown as the most critical parameter change. Window 208 also shows the change in language from Spanish to English. As indicated above with reference to FIG. 9, profile set 147 currently present on pump 1 is also being replaced by profile set 143 of configuration file 141. The operator must use scrollbar 232 to view these basal rate profile changes.

Figure 13:
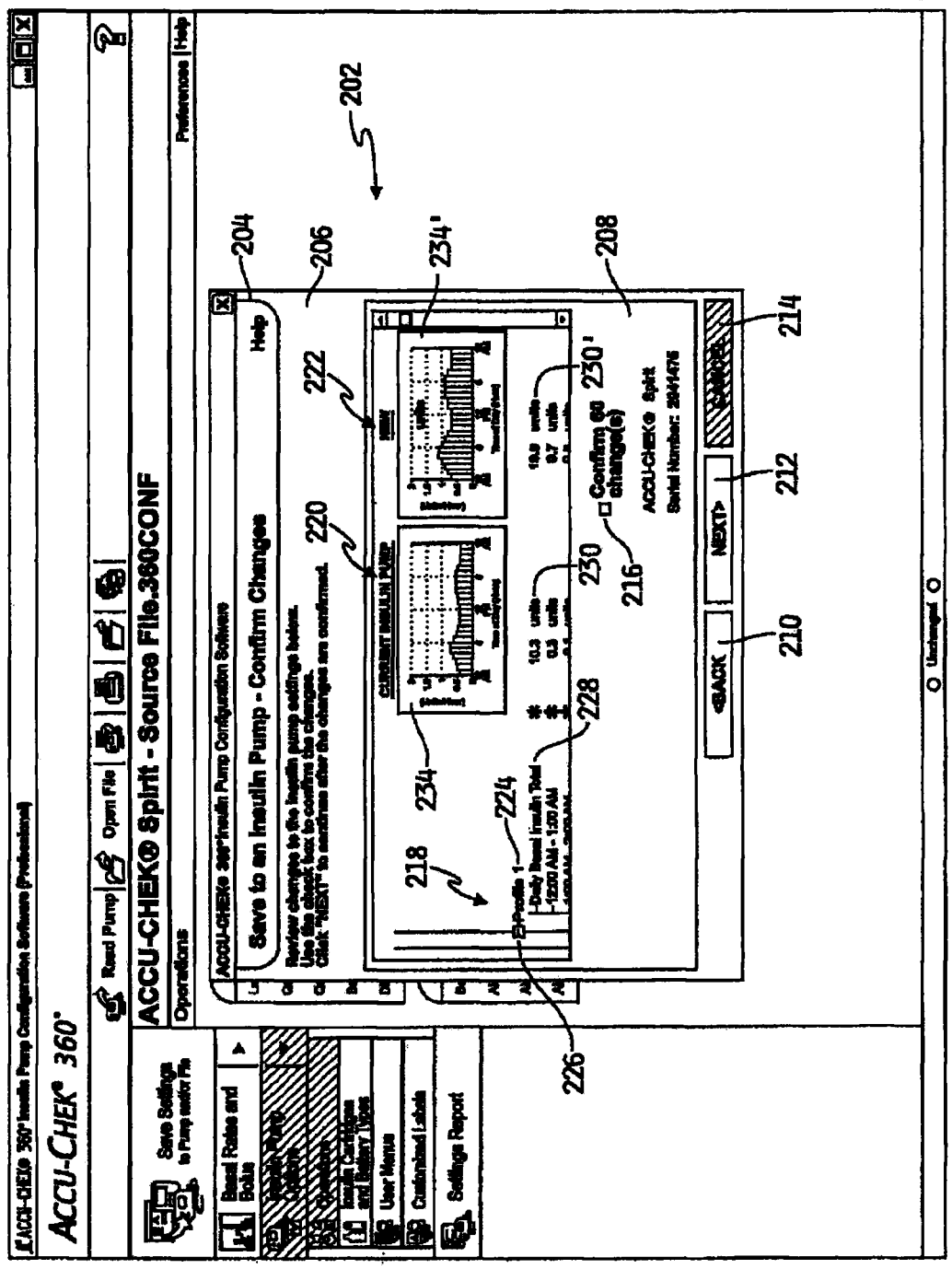

As shown in FIG. 13, when the operator uses scrollbar 232 to scroll upwardly, the operator may review changes about to be made to profile set 147. In this view, new information column 222 includes a thumbnail image 234' that corresponds to thumbnail image 166A of FIG. 6 (i.e., profile 1 of profile set 143). Current pump information column 220 includes a thumbnail image 234 that graphically depicts the data associated with basal rate profile 1 of profile set 147 on pump 1.

Figure 14:
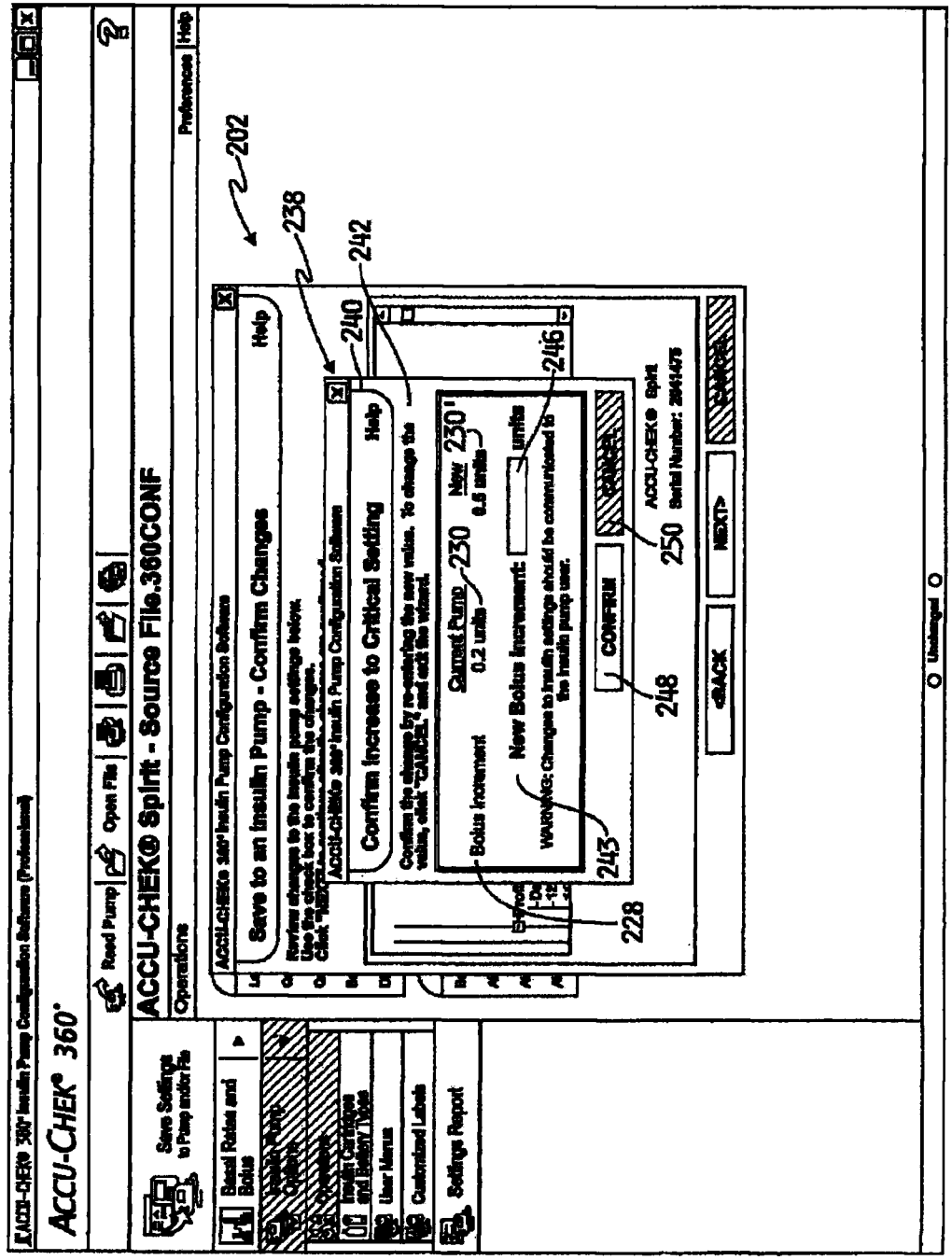
FIG. 14 is a screenshot including a critical change confirmation box for a bolus increment change.

After the operator reviews the changes about to be made to configuration file 145 by comparing the information in the highlighted data fields 230, 230', the operator must check the confirm changes box 216 and activate next button 212. As shown in FIG. 14, this causes software 17 to generate critical change confirmation box 238 which functions as a second verification level before making a change to a pump parameter that may have a serious adverse affect on the user's health. Here, the subject of critical change confirmation box 238 is an increase in the bolus increment. Under delivery of insulin may result in hyperglycemia (high blood glucose levels), which may increase the risk of infection and, if persistent for long periods, may cause damage to the retinas and kidneys, and nerve damage. Over delivery of insulin, on the other hand, may lead immediately to hypoglycemia, which can result in seizures, unconsciousness, and other highly undesirable manifestations of low blood glucose levels.

As shown, critical change confirmation box 238 includes a title bar 240, a message area 242 that instructs the user to re-enter the new data for the parameter about to be changed, a data window 243 showing the parameter name 228, the current pump data 230, and the new data 230', and including a data field 246 for re-entry of the new data. Box 238 also includes a confirm button 248 and a cancel button 250. Instead of requiring the operator to simply check a confirm changes box, which the operator may do without carefully reviewing the parameters being changed, critical change confirmation box 238 requires the operator to type the new data value exactly as it is shown in data field 230' and activate confirm button 248 to approve the change. In this example, the operator types 0.5 into data field 246.

In one embodiment of the present disclosure, activation of cancel button 250 returns the operator to the save settings dialog box 188 of FIG. 10. In an alternate embodiment, only the parameter that is the subject of the current critical change confirmation box 238 is not written to pump 24, but the programming workflow described herein continues.

Figure 15:
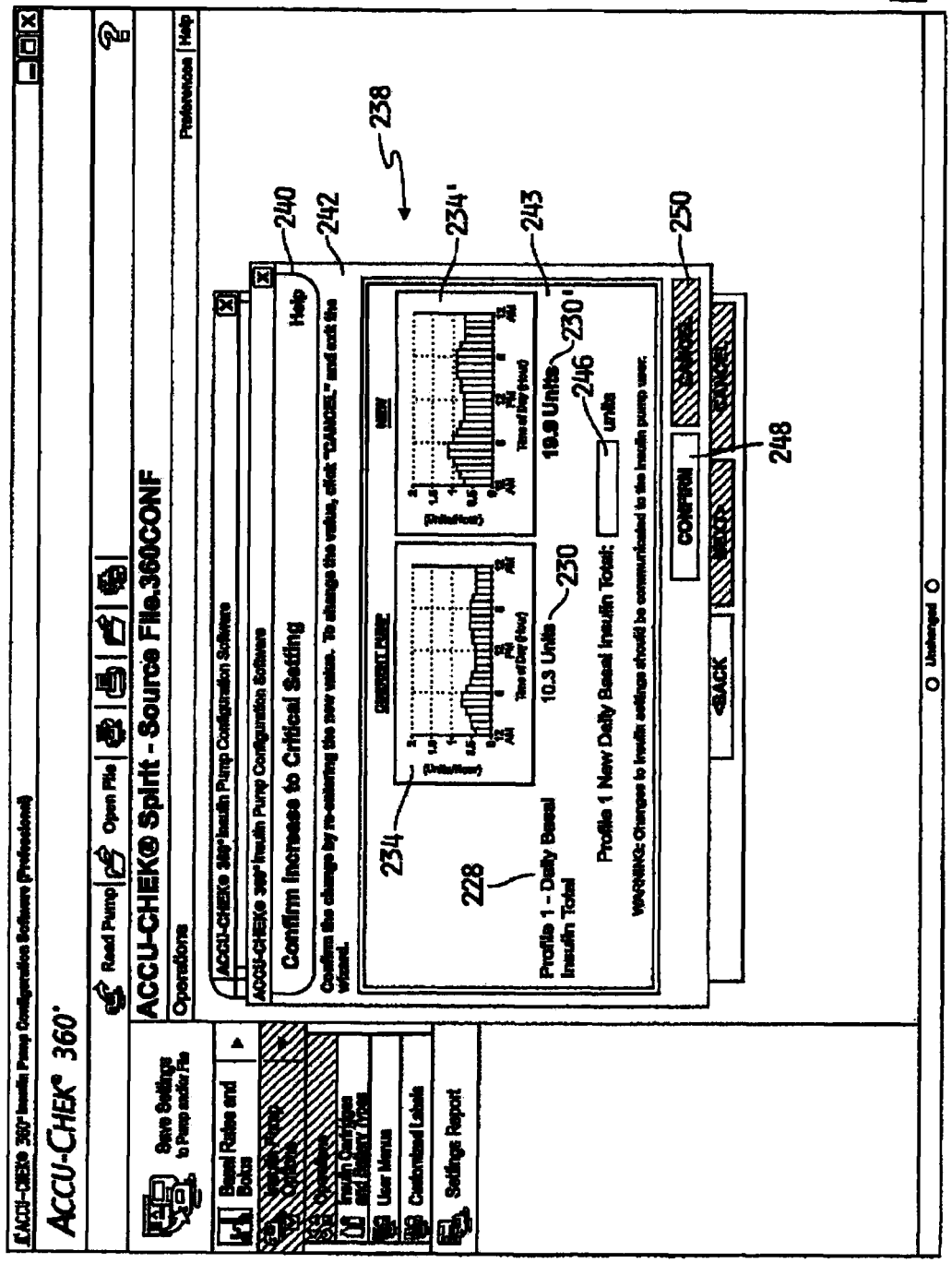
FIGS. 15 through 17 are screenshots including critical change confirmation boxes for basal profile changes.
Figure 16:
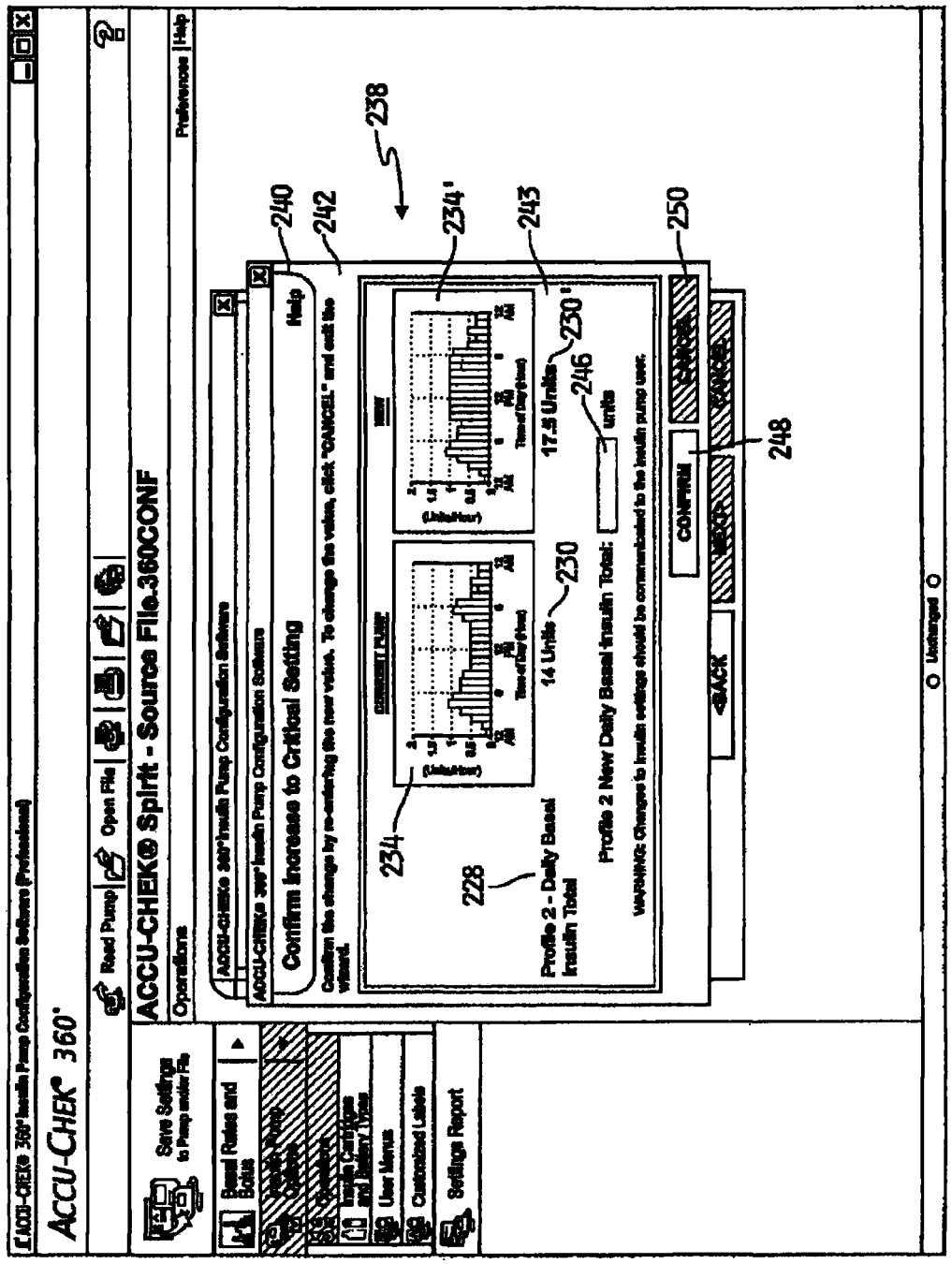
Figure 17:
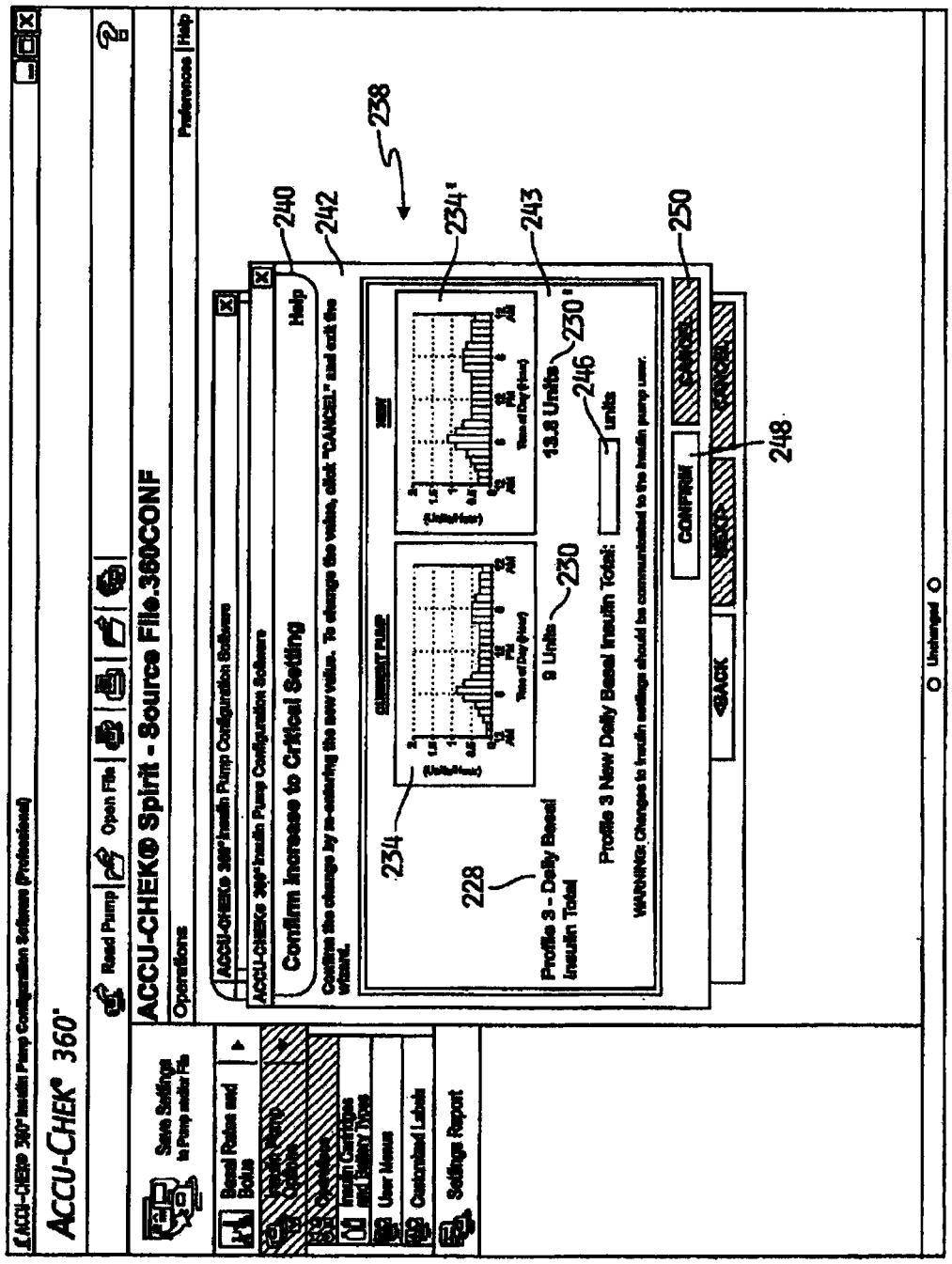

After the operator activates confirm button 248 in FIG. 14, a new critical change confirmation box 238 is displayed as shown in FIG. 15. In FIG. 15, data window 243 includes information, including thumbnail images 234, 234' reflecting the change about to be made to the daily basal insulin total associated with profile 1 of profile set 147. Like an increase in bolus increment, an increase in daily basal insulin total may have a serious adverse affect if accidentally programmed into pump 1. Accordingly, the operator is required to re-enter the new data (i.e., 19.9 units) exactly into data field 246, then activate confirm button 248 to proceed. After entering the new data value and activating confirm button 248, the operator is presented with another critical change confirmation box 238 as shown in FIG. 16. The critical change confirmation box 238 of FIG. 16 includes information similar to that shown in FIG. 15, but reflects the changes about to be made to the daily basal insulin total associated with profile 2 of profile set 147. Again, the operator is required to re-enter the new data (i.e., 17.5 units) exactly into data field 246, then activate confirm button 248 to proceed. After entering the new data value and activating confirm button 248, the operator is presented with yet another critical change confirmation box 238 as shown in FIG. 17. Once again, to change the daily basal insulin total associated with profile 3 of profile set 147, the operator must re-enter the new data (i.e., 13.8 units) exactly into data field 246, then activate confirm button 248 to proceed. Additional critical change confirmation boxes 238 would be presented to the operator if insulin increases for profiles 4 and 5 were to be programmed into profile set 147.

Figure 18:
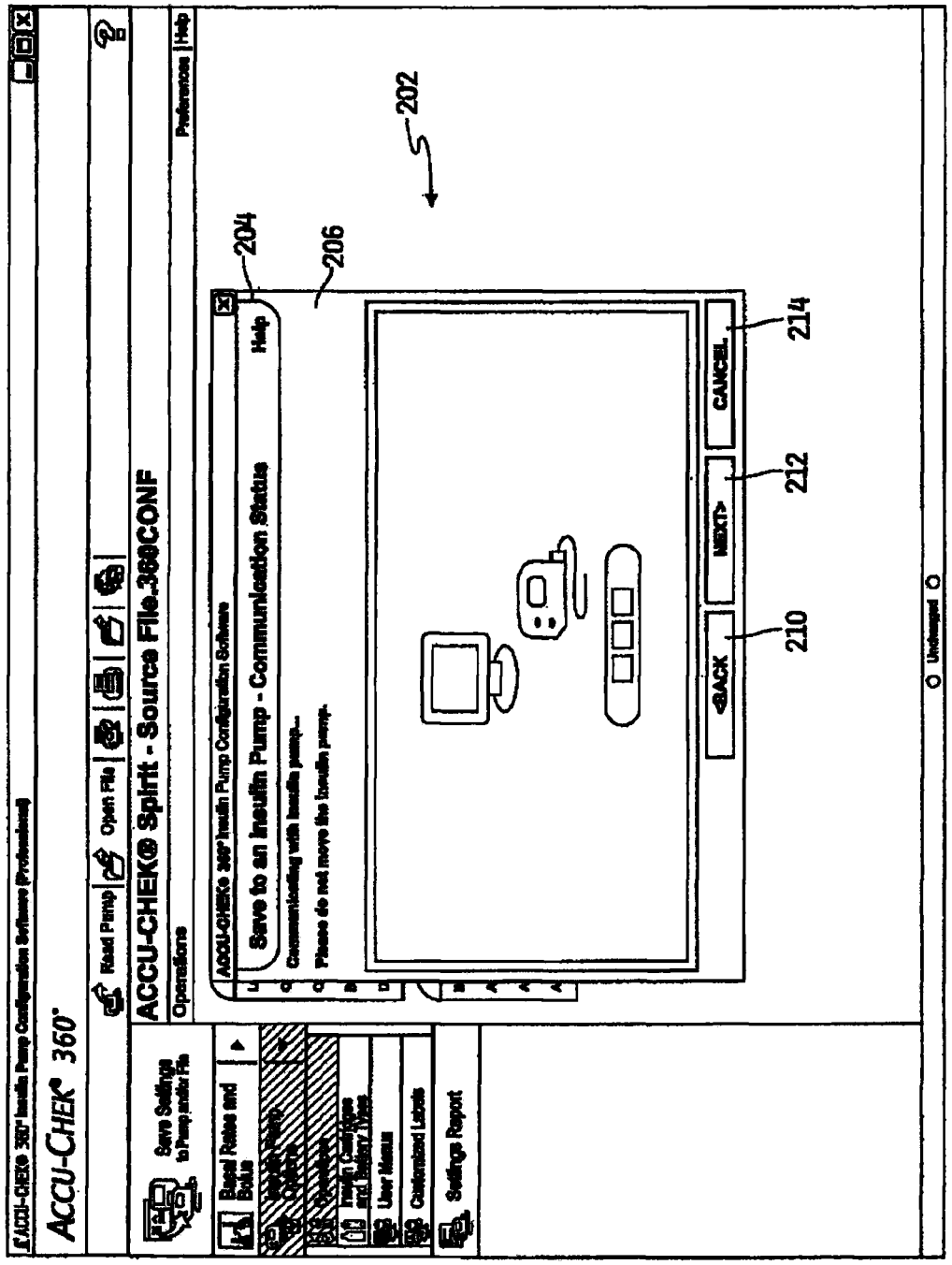
FIGS. 18 and 19 are screenshots similar to that of FIG. 11.
Figure 19:
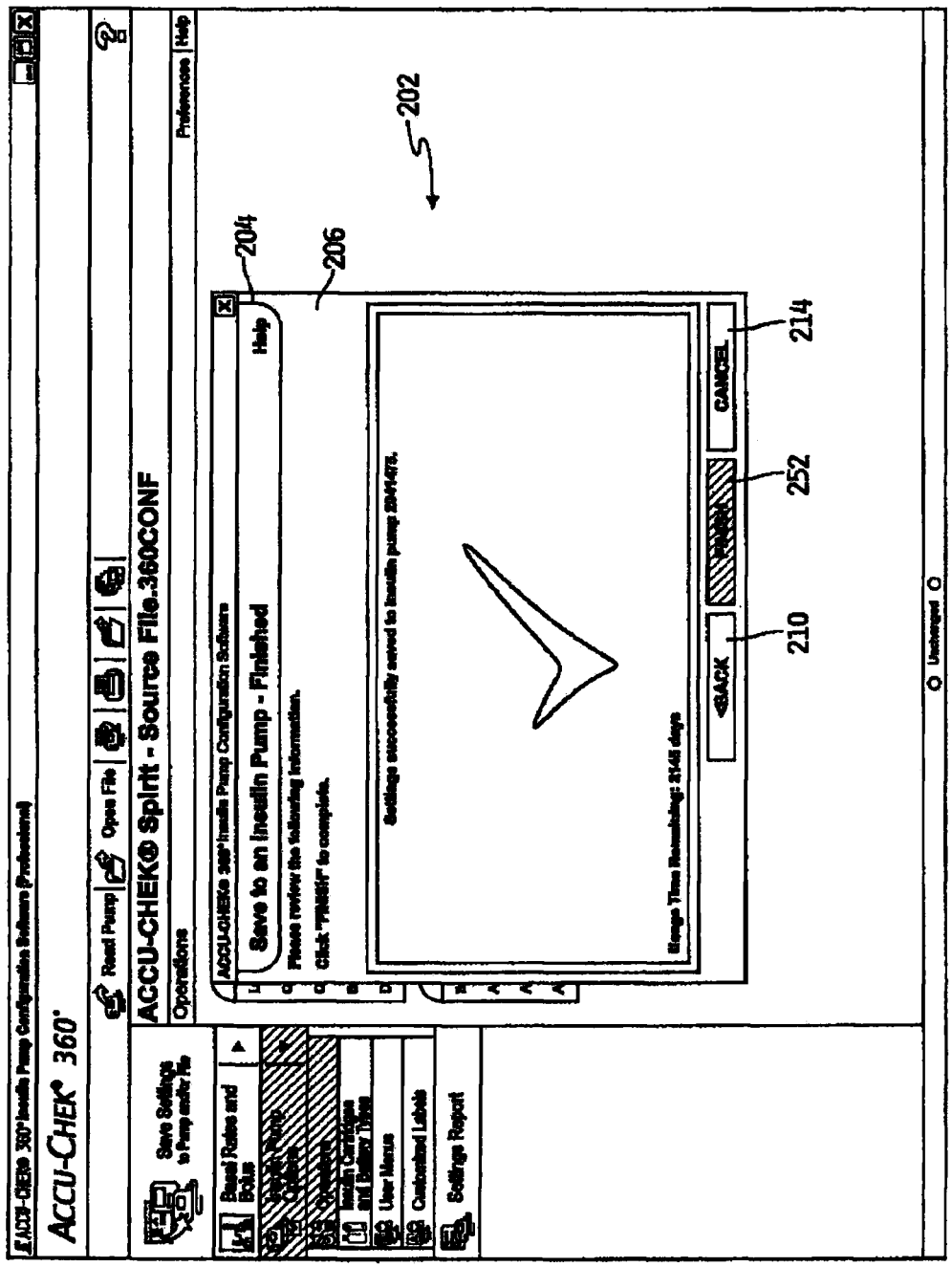
Figure 20:
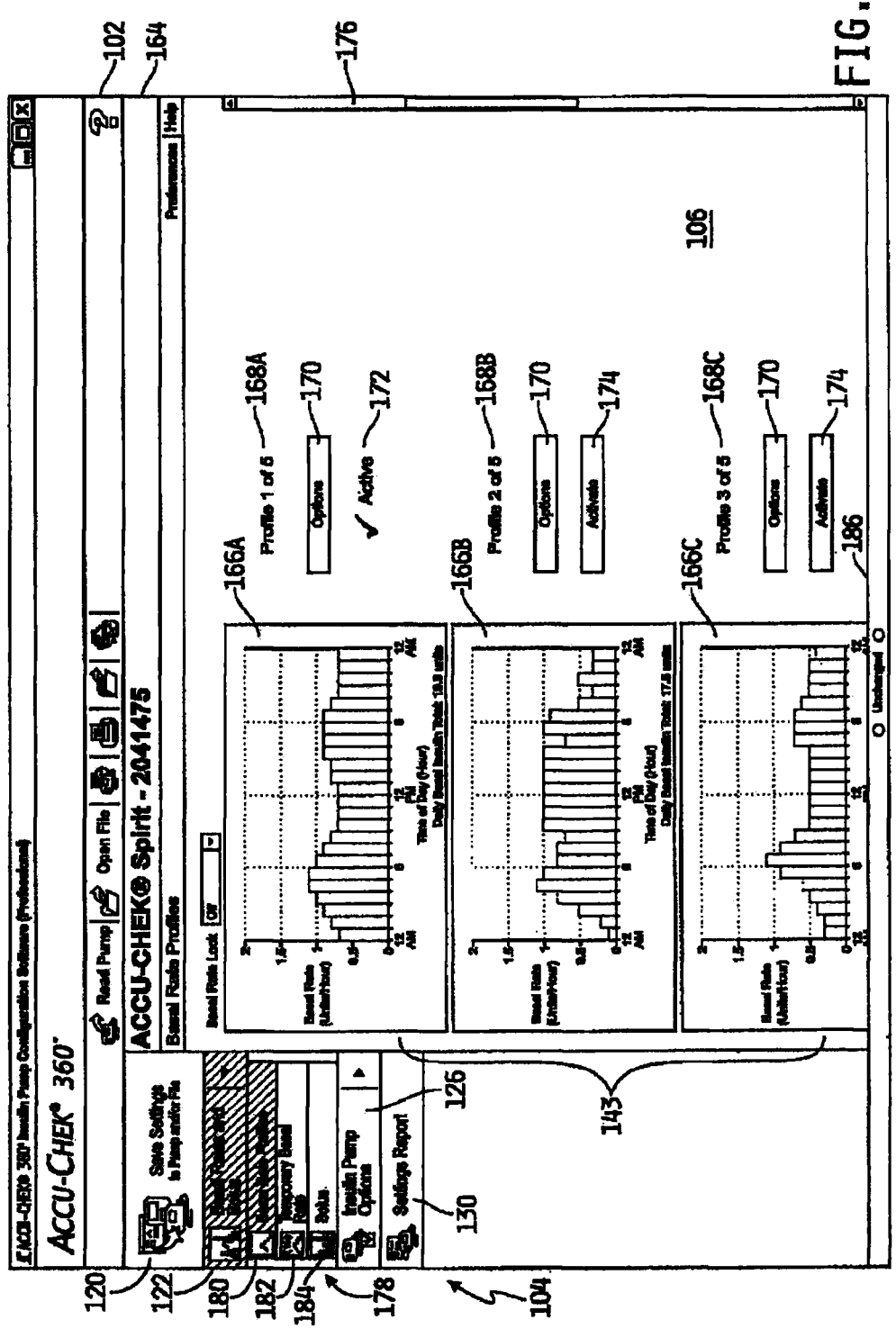
FIG. 20 is a screenshot similar to that of FIG. 6.

Finally, after re-entering the new data (i.e., 13.8 units) into data field 246 of FIG. 17 and activating confirm button 248, communication status dialog box 202 of FIG. 18 is displayed to indicate that configuration file 141 is being programmed into the memory of pump 1. When the programming is complete, communication status dialog box 202 of FIG. 19 is displayed to indicate successful programming. When the operator activates the finish button 252 of dialog box 202, active window 106 of FIG. 20 is displayed. FIG. 20 is similar to FIG. 6, except that the information displayed reflects the newly programmed configuration file present on pump 1 (the now current active file). Accordingly, the serial number for pump 1 is displayed in title bar 164. Otherwise, the two figures are identical as the information (e.g., thumbnail images 166A-C) of the newly programmed configuration file is identical to that of previously active file 141.

As described above, to replace configuration file 145 of pump 1 with configuration file 141, the operator is required to check confirm box 216 and activate next button 212 (FIG. 12), and re-enter data into data fields 246 (followed by activating confirm button 248) for four critical data changes (i.e., bolus increment (FIG. 14), daily basal insulin total for profile 1 (FIG. 15), daily basal insulin total for profile 2 (FIG. 16), and daily basal insulin total for profile 3 (FIG. 17).

In the next example programming session, the operator is described as replacing profile set 149 of pump 2 (see FIG. 9) with profile set 143 of configuration file 141. As shown in FIG. 9, pump 2 is currently programmed to use Spanish and provide a bolus increment of 0.2. These parameters are to remain unchanged by the programming. One method for accomplishing a change to only profile set 149 is to activate configuration file 141 in the manner described above, and change the setting for the standard increment for "Quick" Standard Bolus 165 (FIG. 7) from 0.5 to 0.2 and the setting for the language option 177 (FIG. 8) from English to Spanish. After these changes (and any other differences in general configuration data) are complete, the operator may save the modified version of configuration file 141 to pump 2 using save to pump configuration file button 194A (FIG. 10) as described above. This approach, of course, requires the operator to determine the differences in general configuration data between configuration file 141 and configuration file 151, which may be a time consuming, error-prone task. Alternatively, the operator may activate configuration file 141 in the manner described above, and activate save to pump profile set button 194B of FIG. 10. As software 17 will not attempt to program information on pump 2 other than profile set 149 when button 194B is activated, the operator need not determine what other differences (if any) exist between active configuration file 141 and configuration file 151 currently present on pump 2. After the operator activates button 194B of FIG. 10, and next button 212 of communication status dialog box 202 (FIG. 11), communication status dialog box 202 is displayed in active window 106 as shown in FIG. 21.

Figure 21:
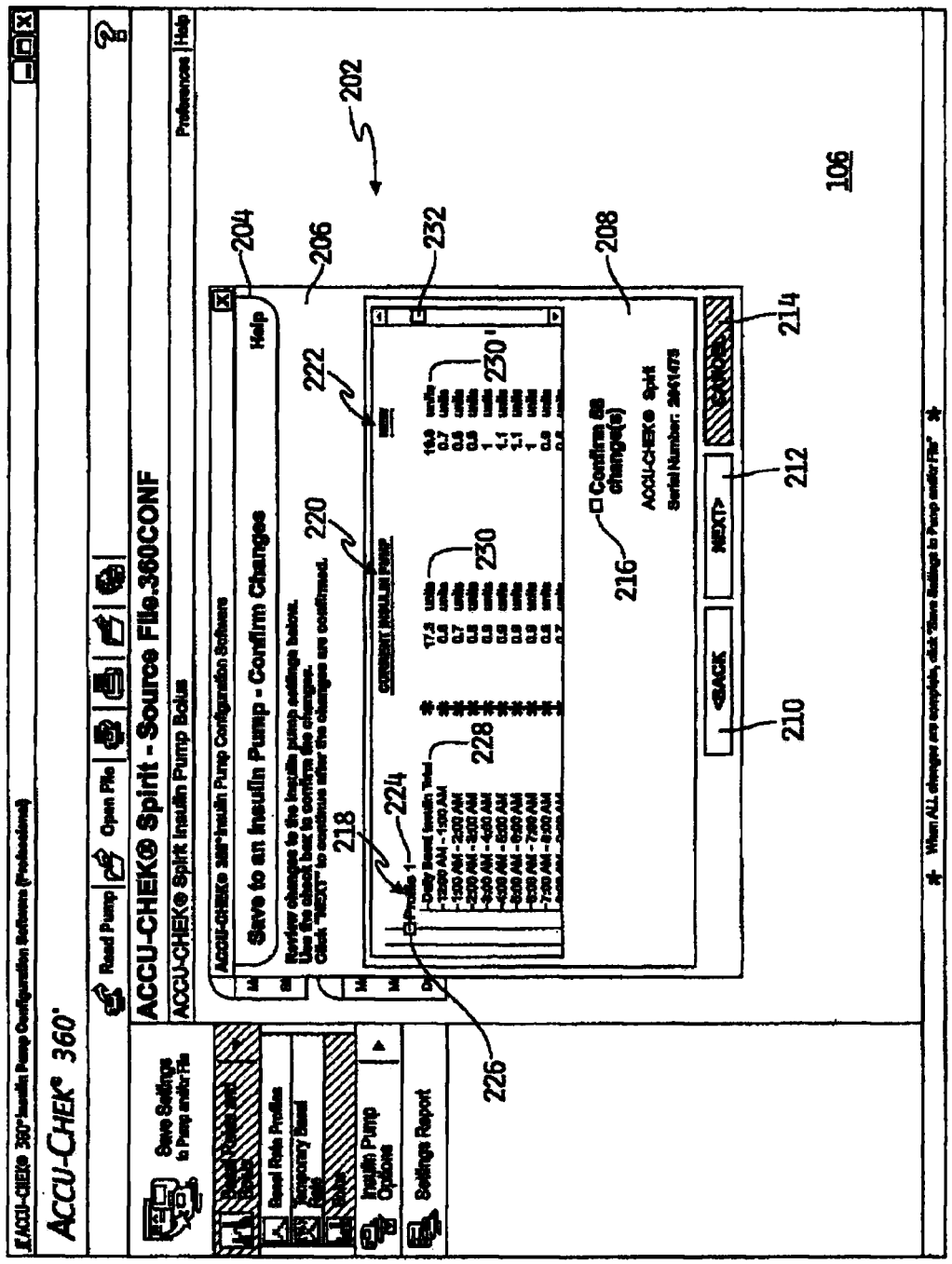
FIG. 21 is a screenshot similar to that of FIG. 11.

The screen depicted in FIG. 21 is similar to the screen depicted in FIGS. 12 and 13. As shown, message area 206 instructs the operator to review the changes that are about to be made to the pump being programmed, and to check the confirm changes box 216 to approve the changes. Configuration file tree structure 218, current pump information column 220, and new information column 222 are automatically scrolled as described above to display (with highlighting) changes to be made to profile 1. The operator can scroll through the information presented in status window 208 using scrollbar 232 to review changes to be made to profiles 2 and 3.

Figure 22:
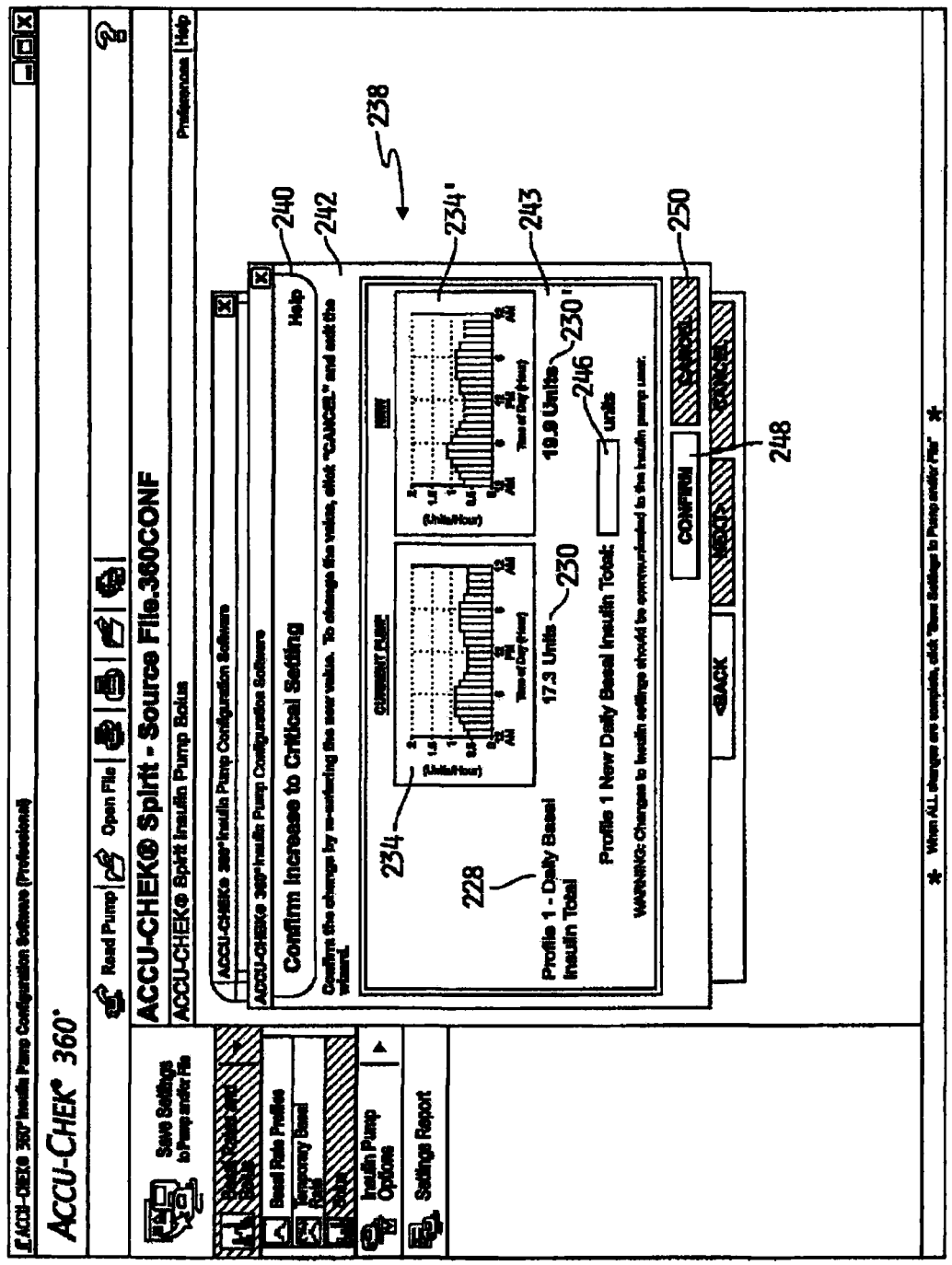
FIG. 22 is a screenshot similar to that of FIG. 15.

After the operator reviews the changes, checks confirm changes box 216, and activates next button 212, critical change confirmation box 238 is displayed as shown in FIG. 22. It should be noted that the confirmation step for changing the bolus increment did not occur in this example as the bolus increment of configuration file 141 is not being written to configuration file 151. Critical change confirmation box 238 is similar to that described above with reference to FIG. 15. It depicts changes about to be made to profile 1 of profile set 149. After the operator re-enters the new daily basal insulin total (i.e., 19.9 units) in data field 246 and activates confirm button 248, the operator is presented with screens corresponding to FIGS. 16 through 20 which guide the operator through critical data changes to profiles 2 and 3 and completion of the programming operation for pump 2.

An alternative approach to programming pump 2 with profile set 143 according to the teachings of the present disclosure is to simply retrieve profile 143 from the source file "Source File.360CONF" using open profile set button 138B or open file icon 110 of FIG. 4. Using open file dialog box 144 of FIG. 5, the operator may simply activate profile set 143 for programming pump 2. In this manner, the operator can avoid programming pump 2 with incorrect general configuration data by accidentally activating save to pump configuration file button 194A (FIG. 10) instead of save to pump profile set button 194B. When only a profile set is made active by software 17 (as opposed to an entire configuration file), configuration file buttons 194A, 196A, and 198A of save settings dialog box 188 are disabled. Once profile set 143 is made active and the operator activates save to pump profile set button 194B, the programming sequence is identical to that described above with reference to FIGS. 21 and 22.

In the next example programming session, the operator is described as replacing individual profile 2 of profile set 153 (hereinafter referred to as individual profile 254—see FIG. 9) on pump 3 with individual profile 2 of profile set 143. As shown in FIG. 9, pump 3 is currently programmed to use Spanish and provide a bolus increment of 0.2. Individual profiles 1 and 3 are depicted as having generalized values of J and L, respectively, which are different from the corresponding generalized values for profiles 1 and 3 of profile set 143. All of these currently programmed parameters are to remain unchanged by the programming. One method for accomplishing a change to only individual profile 254 is to activate configuration file 141 in the manner described above, and change the settings for bolus increment, language, profile 1 and profile 3 to match the settings currently present on pump 3. After these changes are complete, the operator may save the modified version of configuration file 141 to pump 3 using save to pump configuration file button 194A (FIG. 10) as described above. This approach, of course, requires the operator to determine the differences between configuration file 141 and configuration file 155 and make the necessary changes, which may be a time consuming, error-prone task.

Alternatively, the operator may activate configuration file 141 in the manner described above, and activate save to pump individual profile button 194C of FIG. 10. As software 17 will not attempt to program information on pump 3 other than individual profile 254 when button 194C is activated, the operator need not determine what other differences (if any) exist between active configuration file 141 and configuration file 155 currently present on pump 3. After the operator activates button 194C of FIG. 10, and next button 212 of communication status dialog box 202 (FIG. 11), communication status dialog box 202 is displayed in active window 106 as shown in FIG. 23.

Figure 23:
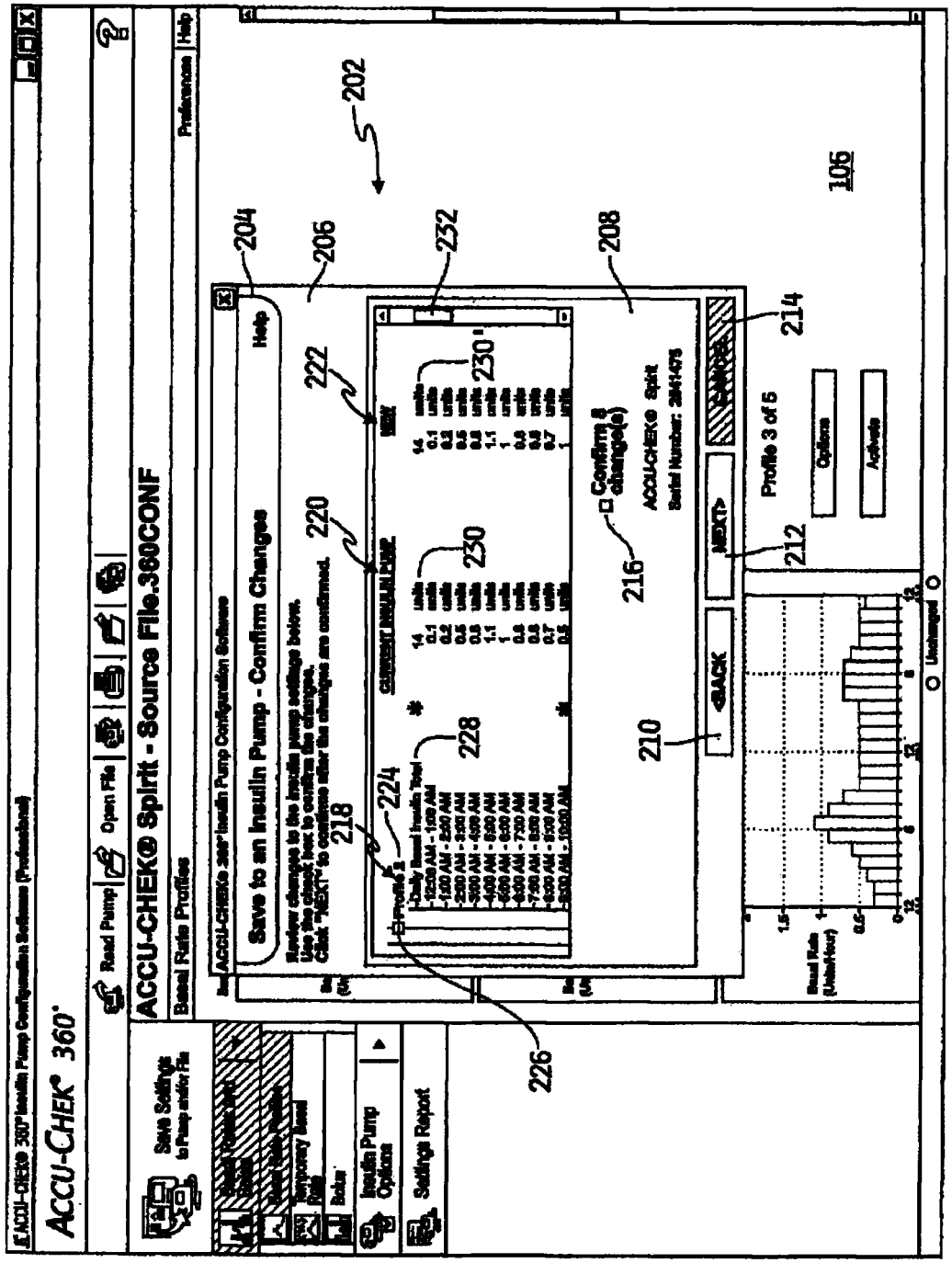
FIG. 23 is a screenshot similar to that of FIG. 11.
Figure 24:
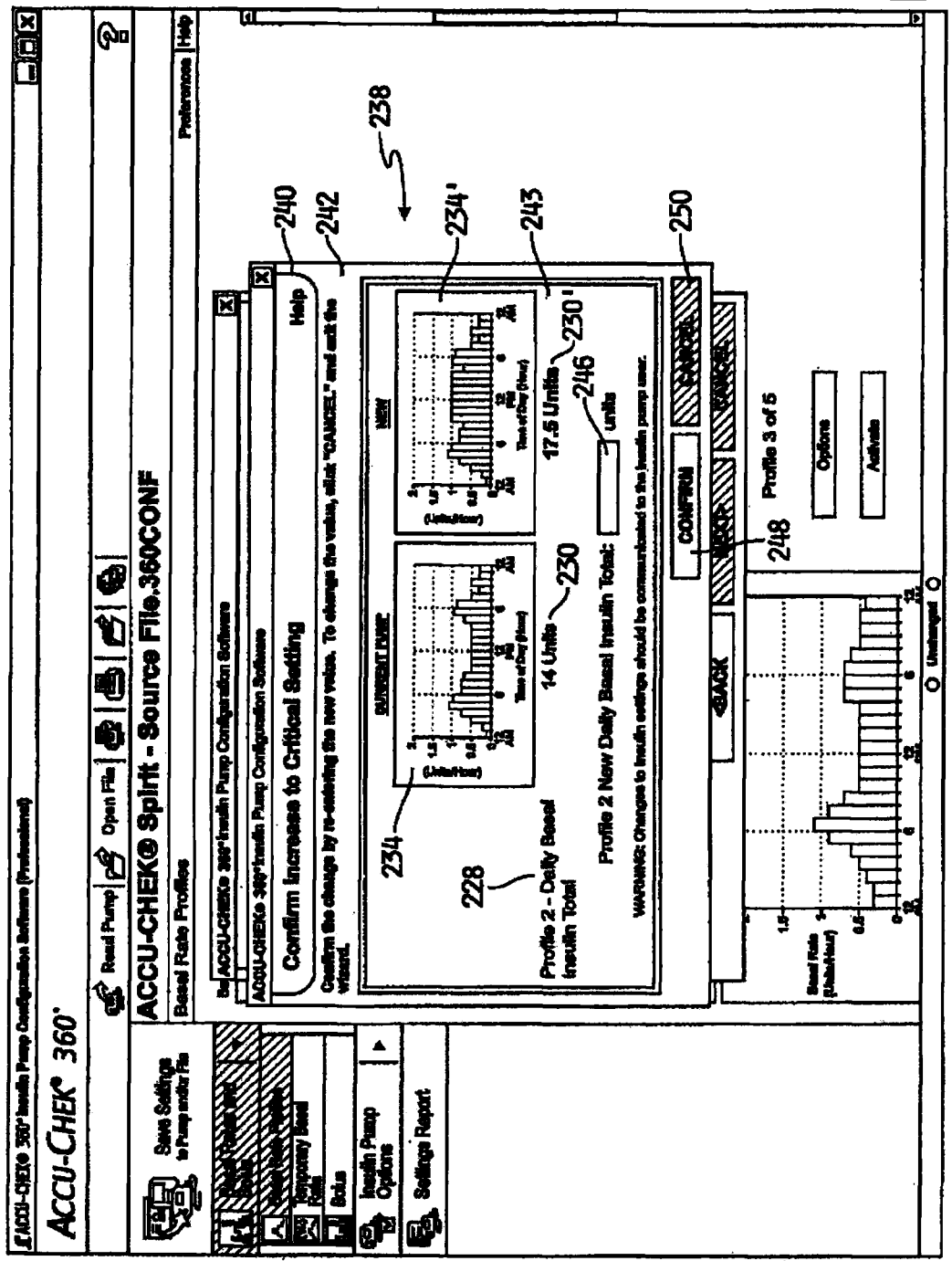
FIG. 24 is a screenshot similar to that of FIG. 16.

The screen depicted in FIG. 23 is similar to the screen depicted in FIGS. 12 and 13. Here, however, the only highlighted changes are those to be made to individual profile 254. After the operator reviews the changes, checks confirm changes box 216, and activates next button 212, critical change confirmation box 238 is displayed as shown in FIG. 24, which is similar to the display depicted in FIG. 16. This is the only critical change confirmation box 238 presented to the operator in this programming example as only individual profile 254 is being programmed. After the operator re-enters the new daily basal insulin total (i.e., 17.5 units) in data field 246 and activates confirm button 248, the operator is presented with screens corresponding to FIGS. 18 through 20 which complete the programming operation for pump 3.

An alternative approach to programming pump 3 with individual profile 2 of profile set 143 according to the teachings of the present disclosure is to simply retrieve individual profile 2 from the source file "Source File.360CONF" using open individual profile button 138C or open file icon 110 of FIG. 4. Using open file dialog box 144 of FIG. 5, the operator may simply activate individual profile 2 for programming pump 3. In this manner, the operator can avoid inadvertently attempting to program pump 3 with general configuration data or changes to other individual profiles by accidentally activating save to pump configuration file button 194A or save to pump profile set button 194B (FIG. 10) instead of save to pump individual profile button 194C. When an individual profile is made active by software 17 (as opposed to an entire configuration file or a profile set), configuration file buttons 194A, 196A, and 198A and profile set buttons 194B, 196B, and 198B of save settings dialog box 188 are disabled. Once individual profile 2 of profile set 143 is made active and the operator activates save to pump individual profile button 194C, the programming sequence is identical to that described above with reference to FIGS. 23 and 24.

In the next example programming session, the operator is described as replacing configuration file 157 of pump 4 (FIG. 9) with configuration file 141. Assume in this example that the operator really only intends to replace profile set 159 with profile set 143, but rather than using save to pump profile set button 194B (FIG. 10), the operator activates save to pump configuration file button 194A. As shown in FIG. 9, pump 4 is currently programmed to use Spanish and provide a bolus increment of 0.5. All of individual profiles 1 through 3 are depicted as being different from the corresponding individual profiles of profile set 143.

Figure 25:
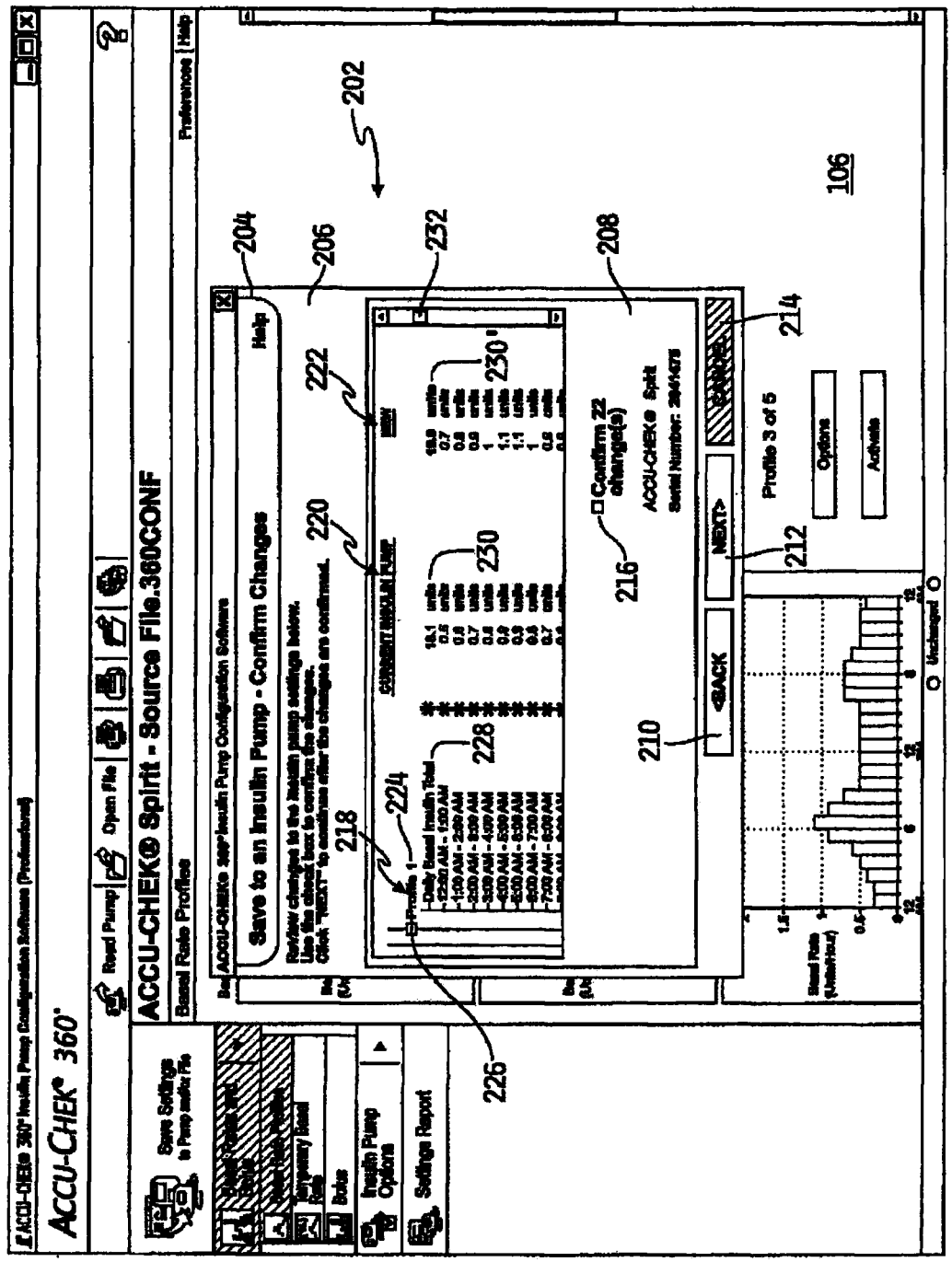
FIGS. 25 and 26 are screenshots similar to that of FIG. 11.
Figure 26:
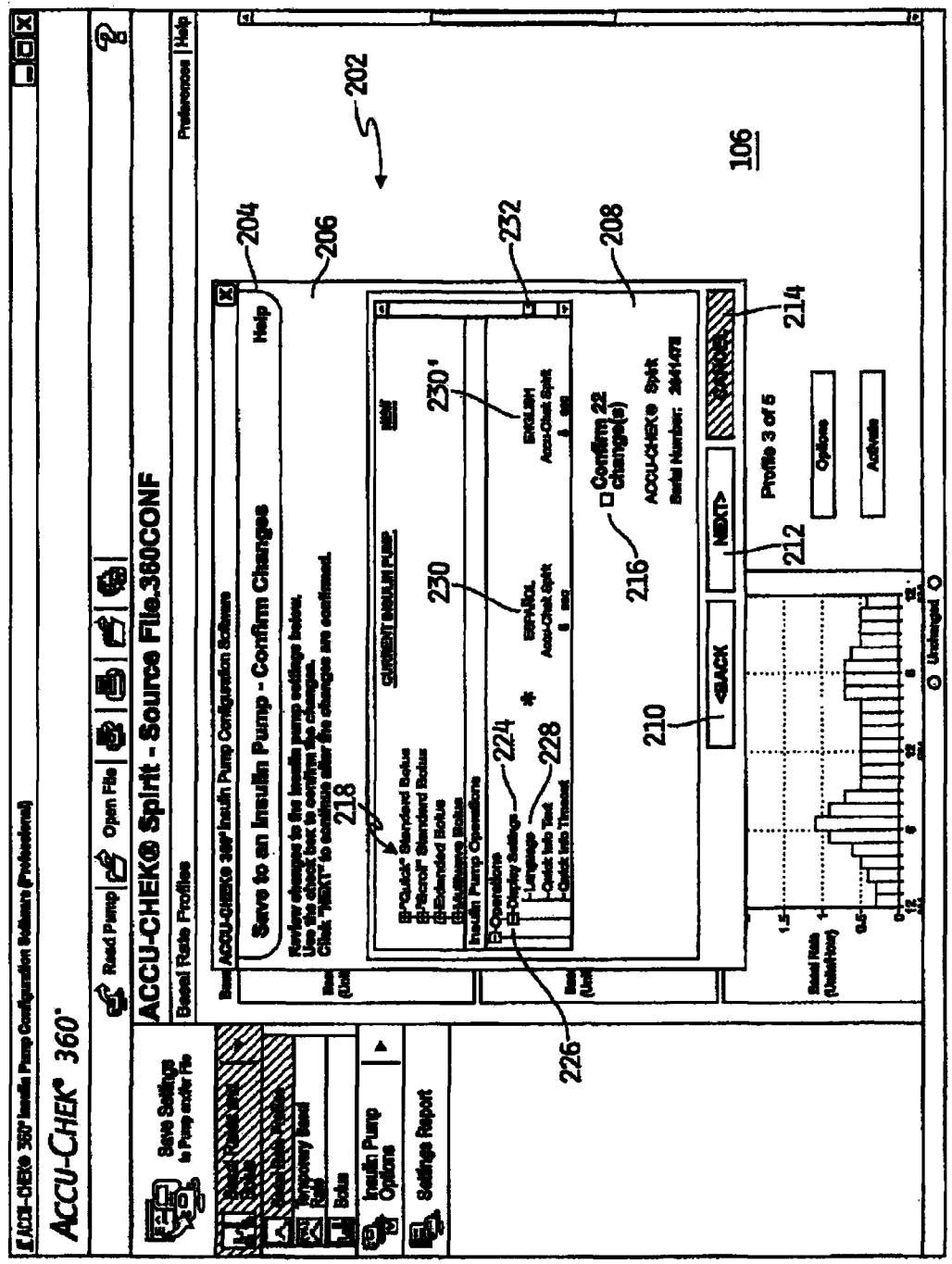

After the operator retrieves configuration file 141 in the manner described above, the operator activates save to pump configuration file button 194A (FIG. 10), instead of save to pump profile set button 194B. Software 17 then communicates with pump 4 (FIG. 11) and displays communication status dialog box 202 as shown in FIG. 25. Again, the most important changes to be made are automatically positioned for viewing in status window 208. Here, the changes to profile 1 are shown. If the operator used scrollbar 232 to scroll the content of status window 208, the operator could determine that the language option is about to be changed by viewing the screen as depicted in FIG. 26. In that case, the operator may realize that a language change is not desired, activate cancel button 214, and change the language option as described above before re-attempting to program pump 4.

For purposes of this example, assume that the operator scrolls down to review the changes to be made to profiles 2 and 3, and checks confirm changes box 216 without scrolling farther down to notice the language change. After activating next button 212 of FIG. 25, the operator is presented with critical change confirmation boxes 238 similar to those depicted in FIGS. 15 though 17 for confirmation of increases to be made to the profiles of profile set 159. After that, the programming process as described with reference to FIGS. 18 through 20 would be carried out, and the programming operation completed. Unfortunately, however, as this example illustrates, the operator inadvertently changed the language option of pump 4 from Spanish to English. As a result, the pump user, who may have visited the operator's office to have pump 4 programmed, may realize later in the day (after leaving the operator's office) that he or she is unable to operate pump 4.

Had the operator simply activated save to pump profile set button 196B, the above-described programming error would have been avoided. Of course, the operator could also have activated only profile set 143 (instead of entire configuration file 141) using open profile set button 138A (FIG. 4) and caused configuration file buttons 194A, 196A, and 198A to be disabled, thereby preventing the above-described error. It should further be understood with respect to all of the above-described examples, the operator may have chosen to activate configuration files, profile sets, or individual profiles from the pumps to be programmed using buttons 136A-C of read pump area 136, rather than retrieving configuration file 141 (or some portion thereof) from memory 15. Upon activating the pump information, the operator may make the desired modifications in the manner described above, and re-program the pump using buttons 194A-C of save to pump area 194 (FIG. 10).

Finally, with reference to FIG. 10, it should be understood that in addition to saving information to a pump as described above, the teachings of the present disclosure permit saving an active information set (i.e., a configuration file, a profile set, or an individual profile) to either a file or to both a pump and a file in one operation. Upon activating any one of buttons 196A-C of save to file area 196, the operator is presented with a screen similar to that depicted in FIG. 5 except that open file dialog box 144 is replaced with a similar save file dialog box (not shown). The operator can then select/define the location, name, and type of the file to be saved. Upon activating any one of buttons 198A-C of save to both area 198, the operator is first presented with the screen including a save file dialog box (not shown). After completing the file save, the operator is then guided through the various pump programming steps described above. In this manner, a backup file of the information being saved to a pump is made as part of the pump programming workflow, thereby reducing the steps required of the operator.

One aspect of the configuration software 17 enables the patient or their healthcare provider to customize the names of the basal profiles for ease of use. In one embodiment, a set of predefined basal profiles are stored on the computing device 12 and accessible to the configuration software 17. Each of the predefined basal profiles may be assigned a generic default name, such as Profile 1, Profile 2, etc. When configuring a patient's configuration file, one or more of the predefined basal profiles may be assigned to the patient's configuration file 141. In doing so, the healthcare provider may customize the parameters of the profile to the particular patient, including the name of the profile. Rather than use a generic default name, it is more intuitive for the name of the insulin delivery profile to correlate to the use case it is tailored to address. For example, a basil profile tailored for weekday use may be named 'weekday profile'; whereas, a basil profile tailored for weekend use may be named 'weekend profile'. While reference is being made to basal profiles, it is readily understood that the concepts regarding customizing names extend to other types of insulin delivery profiles (e.g., a custom bolus profile) as well as other types of parameters.

Figure 27:
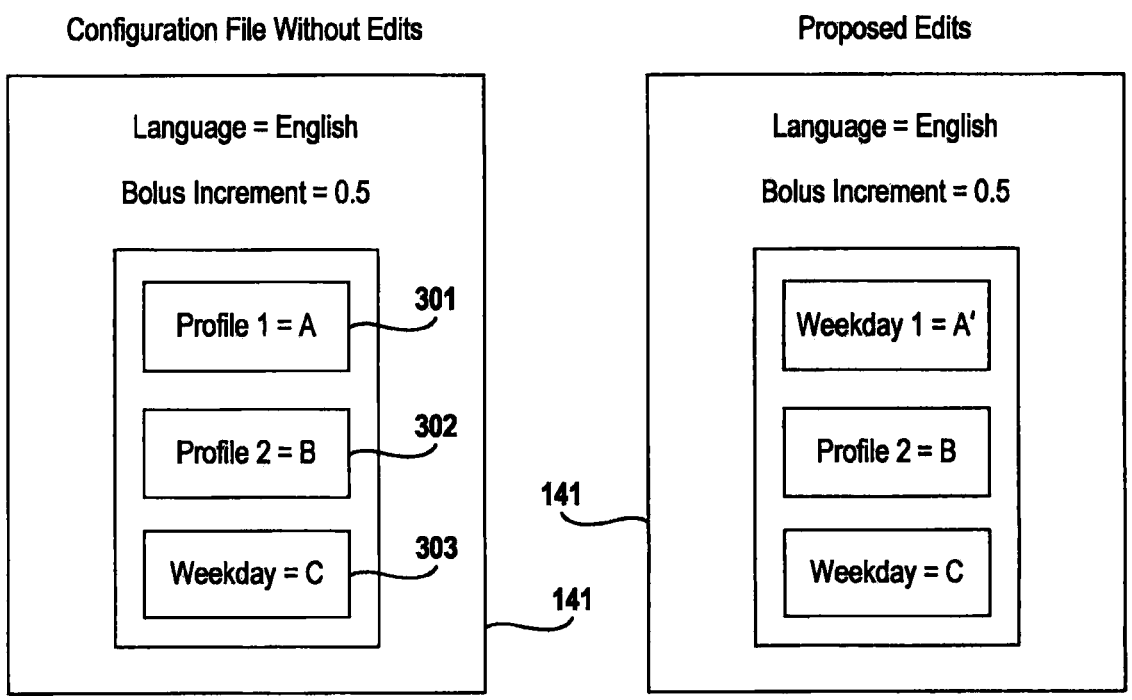
FIG. 27 is a diagram illustrating a proposed name change of a profile in a configuration file.

FIG. 27 illustrates a proposed change to the name of an individual profile associated with configuration file 141. In particular, the user is proposing to change the name of a first basal profile 301 from 'Profile 1' to 'Weekday Profile'. In the exemplary embodiment, the user may change the name of a basal profile at 224 of the screen depicted in FIG. 23. After the user review the change to the name as well as any other profile changes, checks confirm changes box 216 and activates the next button 212, critical change confirmation box 238 may be displayed as shown in FIG. 24. In the exemplary embodiment, the user is required to re-enter the new daily basal insulin total in data field 246. It is envisioned that the user may also be required re-enter the name of the basal profile. Once the user activates the confirm button 248, the process for programming operation of the pump 3 is initiated.

Figure 28:
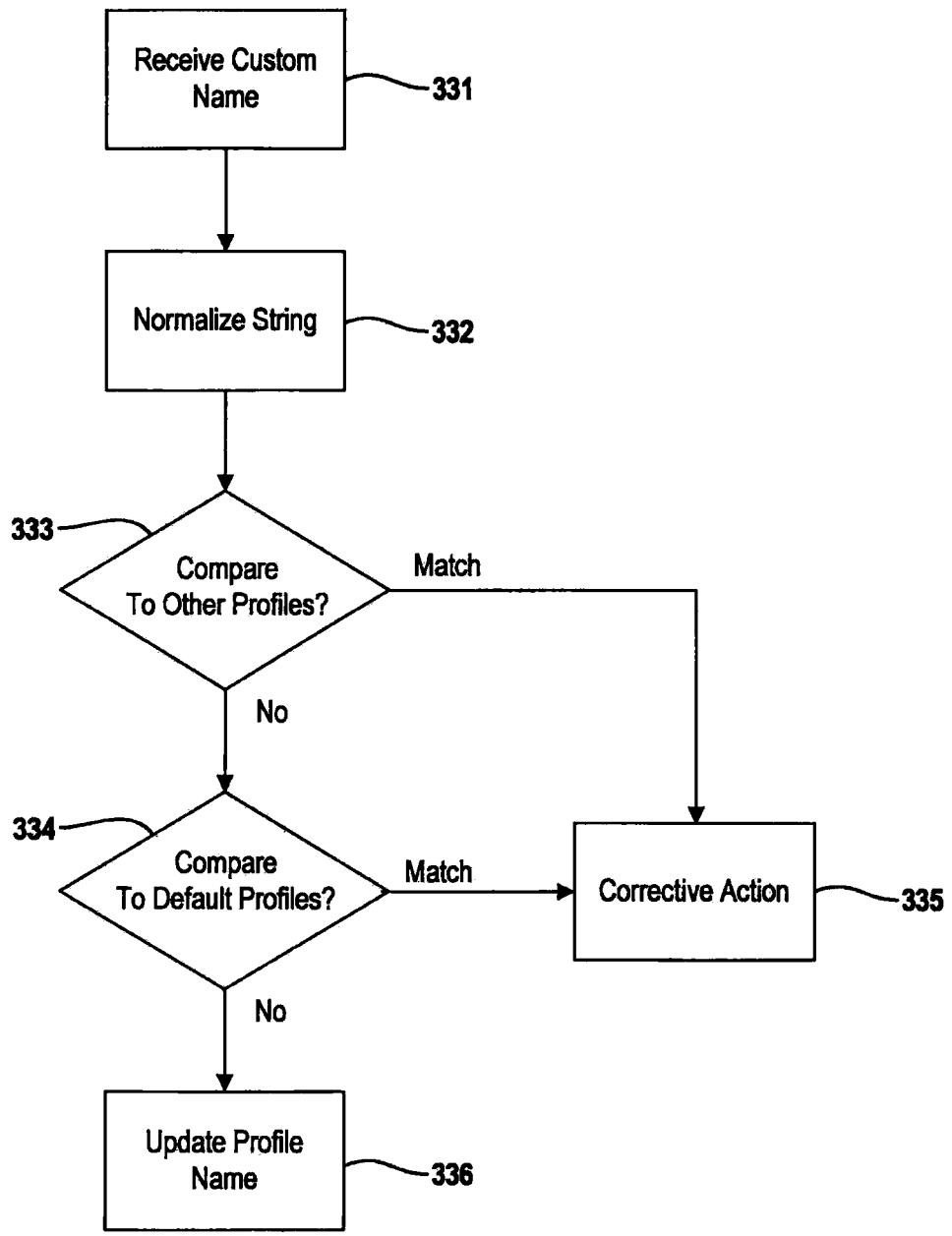
FIG. 28 is a flowchart depicting an exemplary technique for validating changes to profile names.

Prior to programming the pump, the configuration software 17 ensures that the change of the profile name is unique in relation to the other profile names accessible to the patient as will be described in relation to FIG. 28. Upon receiving a change in the profile name at 331, the edited profile name is checked against other profile names residing on the insulin pump and thus accessible to the patient for use. To do so, the string of characters which comprise the profile name are first normalized at 332 in accordance with a rule set. In an exemplary embodiment, the rule set may specify that spaces be removed from the string of characters and/or that characters in the string of characters be converted to lower case. In addition, the rule set may specify that the term 'profile' be removed from the string. For example, an input string of 'Weekday Profile' may be changed to a normalized string of 'weekday'. The normalized string is then used to verify the uniqueness of the profile name. Normalization ensures that two profile names are not substantially similar so as to avoid a mistaken selection by the patient or their caregiver. Other types of normalizing rules are contemplated by this disclosure and fall within the broader aspects of this disclosure.

The normalized string of characters is compared at 333 with the names for each of the other insulin delivery profiles. With reference to FIG. 27, the normalized string of 'weekday' is compared to both the second and third basal profiles 302, 303. For comparison purposes, it is understood that the character string for the second and third basal profiles 302, 303 are also normalized in accordance with the rule set. That is, the string of 'Profile 2' for the second basal profile 302 is normalized to 'profile2'; whereas, the string of 'week day' for the third basal profile 303 is normalized to 'weekday'. In the exemplary embodiment, the normalized strings for the insulin delivery profiles are stored along with the non-normalized profile names. In other embodiment, the names of the other insulin delivery profile names may be normalized dynamically as needed for comparison.

When the normalized input string matches one of the other insulin delivery profiles, a corrective action is taken as indicated at 335. In one exemplary embodiment, the insulin pump user is prompted to change the input string of characters to a different name. The user may be prompted by a message displayed on a display of the insulin pump, where the message may include the name as well as other information for the matching profile. The display may also provide a field to input an alternative name selection for either the input string (i.e., the first basal profile 301) or the matched profile (i.e., the third basal profile 303). It is understood that the alternative name selection is also subject to the verification process described here. In another exemplary embodiment, the normalized input string may be replaced with a default name to ensure that the customized profile is updated and saved into memory without being lost.

Figure 29:
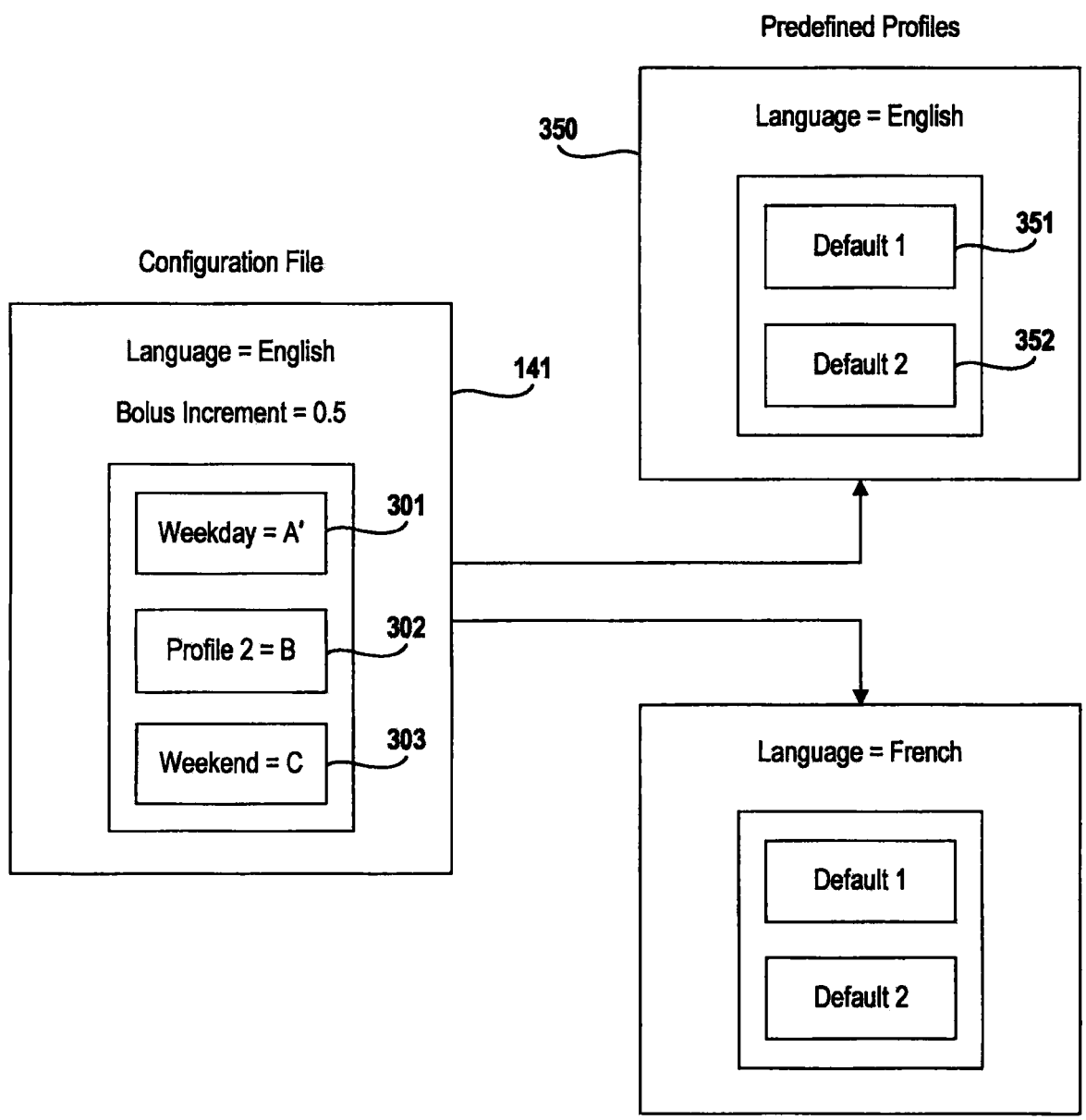
FIG. 29 is a diagram illustrating how a proposed name change may be validated in relation to predefined profile names.

When the normalized input string does not match one of the names for the other insulin delivery profiles, it is then compared at 334 with a set of predefined insulin delivery profiles as illustrated in FIG. 29. In some embodiments, the insulin pump is configured with one or more predefined insulin delivery profiles 350 which may have been defined, for example by a physician for treating a particular situation. Each of the predefined insulin delivery profiles has a default name and is made available to the patient for use. When changing a name of an insulin delivery profile it is preferable that the new name not match a default name for one the predefined profiles. Accordingly, the normalized input string is compared at the time of proposed name change. For example, the name of the second basal profile 302 should not be changed from 'profile 2' to 'default 2'. In this example, the name of the second basal profile 302 would correspond to the second predefined profile 352.

In some embodiments, it is envisioned that the comparison is not made at the time the name of the profile is changed but rather when a predefined insulin delivery profile is selected or enabled by the patient for use. During use, the patient may enable one of the predefined insulin delivery profiles for use by the patient. In this case, the selected profile is added to the patient's active configuration file 141. Before enabling the selected profile, the default name for the predefined insulin delivery profile is compared to the insulin delivery profiles in the manner described above, thereby ensuring uniqueness for the enabled profile.

In other embodiments, the insulin pump may be configured with two or more different language. Each language has a language file residing on the insulin pump, where the language file stores the words and phrases used by the configuration software. For example, the insulin pump may be configured with English and French language files. These files can include the names for the predefined insulin delivery profiles as shown in FIG. 29. In this example, the name for the first basal profile 351 is provided in English and French (i.e., default 1 and defaut 1). Likewise, the name of the second basal profile 352 is provided in English and French. In such embodiments, the normalized input string for the profile being changed is compared to the active language file as well as to the other languages supported by the insulin pump. In other words, if the patient elects to change the name of the second basal profile from 'profile 2' to 'defaut 2', a match will be found in the French language file and an appropriate corrective action may be taken. In this way, names are not duplicated across languages.

When the normalized input string matches one of the default names for the predefined insulin delivery profiles, the user is prompted to take a corrective action at 335. For example, the insulin pump user is prompted to change the input string of characters to a different name. The user may be prompted by a message displayed on a display of the insulin pump, where the message may include the name as well as other information for the matching profile. The display may also provide a field to input an alternative name selection for either the input string or the matched profile. Conversely, if the normalized input string does not match a default name for the one of the predefined insulin delivery profiles, the name of the profile is updated at 336. In this way, the customized name is ensured of being unique in relation to the names of the other profiles accessible to the patient on the insulin pump.

Techniques for customizing names of insulin delivery profiles may be extended to names of other types of parameters found on an insulin pump. Moreover, these techniques may also be extended to parameters found on other types of medical devices, such as a glucose meter, a handheld diabetes management device or the like. Exemplary parameters found on a glucose meter may include but are not limited to medication reminders, custom health events and custom data reminders.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A computer-implemented method for customizing names of insulin delivery profiles for improved patient safety, comprising:
receiving, by a configuration device, a string of characters to serve as a name for a given insulin delivery profile, where the insulin delivery profile includes at least one parameter pertaining to insulin delivery by an insulin pump and is one of a plurality of insulin delivery profiles associated with a given patient;
normalizing, by the configuration device, the string of characters by changing one or more of the characters in the string of characters in accordance with a rule set;
comparing, by the configuration device, the normalized string of characters with names for each of the plurality of insulin delivery profiles;
prompting, by the configuration device, a user to change the normalized string of characters by displaying a message on the display of the configuration device, the prompting being performed in response to a match between the normalized string of characters and at least one of the names of the plurality of insulin delivery profiles;
updating, by the configuration device, the name of the given insulin delivery profile in a pump configuration file residing on the configuration device with the normalized string of characters, wherein the name of the given insulin delivery profile differs from name of the pump configuration file and updating occurs when the normalized string of characters is unique in relation to the names of the plurality of insulin delivery profiles and in response to the comparison step, the steps of normalizing, comparing, prompting and updating being performed solely by computer executable instructions being executed by a computer processor in the configuration device;
downloading the pump configuration file from the configuration device to an insulin pump; and
delivering insulin, by the insulin pump, to the given patient in accordance with a parameter from a selected one of the plurality of insulin delivery profiles in the pump configuration file.

2. The method of claim 1 further comprises replacing the normalized string of character with a default name and updating the name of the given insulin delivery profile in the pump configuration file with the default name when the normalized string of characters matches a name of one of the plurality of insulin delivery profiles.

3. The method of claim 1 wherein normalizing the string of characters further comprises removing any spaces from the string of characters.

4. The method of claim 1 wherein normalizing the string of characters further comprises converting each character in the string of characters to lower case.

5. The method of claim 1 further comprises
storing, by the configuration device, a set of predefined insulin delivery profiles, each of the predefined insulin delivery profiles having a default name; and
comparing, by the configuration device, the normalized string of names to each of the default names in the set of predefined insulin delivery profiles.

6. The method of claim 1 further comprises delivering insulin, by an insulin pump, to the given patient in accordance with the parameter in the updated given insulin delivery profile.

7. A system comprising an insulin pump and a non-transitory computer readable medium tangibly embodying computer program of instructions executable by a computing device to perform method steps for customizing names of insulin delivery profiles in a configuration file for improved patient safety, wherein the computer program instructions, when executed by a computer processor, performing processing of:
receiving a string of characters from a user to serve as a name for a given insulin delivery profile, where the insulin delivery profile includes at least one parameter pertaining to insulin delivery by an insulin pump and is one of a plurality of insulin delivery profiles associated with a given patient;
normalizing the string of characters from the user by changing one or more of the characters in the string of characters in accordance with a rule set;
comparing the normalized string of characters with names for each of the plurality of insulin delivery profiles;
updating the name of the given insulin delivery profile in a pump configuration file residing on the configuration device with the normalized string of characters when the normalized string of characters is unique in relation to the names of the plurality of insulin delivery profiles;
replacing the normalized string of character with a default name and updating the name of the given insulin delivery profile in the pump configuration file with the default name when the normalized string of characters matches a name of one of the plurality of insulin delivery profiles; and
downloading the pump configuration file to an insulin pump, where the insulin pump is in data communication with the computing device;
wherein the insulin pump is configured to deliver insulin to the given patient in accordance with a parameter in the pump configuration file.

8. The system of claim 7 wherein the method steps further include prompting a user to change the string of characters when the normalized string of characters matches a name of one of the plurality of insulin delivery profiles.

9. The system of claim 7 wherein the method steps further include normalizing the string of characters further comprises removing any spaces from the string of characters.

10. The system of claim 7 wherein the method steps further include normalizing the string of characters further comprises converting each character in the string of characters to lower case.

11. The system of claim 7 wherein the method steps further include storing a set of predefined insulin delivery profiles, each of the predefined insulin delivery profiles having a default name; and comparing the normalized string of names to each of the default names in the set of predefined insulin delivery profiles.

12. A computer-implemented method for customizing names of insulin delivery profiles for improved patient safety, comprising:
receiving, by a configuration device, a string of characters to serve as a name for a given insulin delivery profile, where the insulin delivery profile includes at least one parameter pertaining to insulin delivery by an insulin pump and is one of a plurality of insulin delivery profiles associated with a given patient;
normalizing, by the configuration device, the string of characters by at least one of removing any spaces from the string of characters and converting each character in the string of characters to low case;
comparing, by the configuration device, the normalized string of characters with names for each of the plurality of insulin delivery profiles;
replacing, by the configuration device, the normalized string of characters with a default name and updating the name of the given insulin delivery profile in the pump configuration file with the default name when the normalized string of characters matches a name of one of the plurality of insulin delivery profiles;
updating, by the configuration device, the name of the given insulin delivery profile in a pump configuration file residing on the configuration device with the normalized string of characters when the normalized string of characters is unique in relation to the names of the plurality of insulin delivery profiles, wherein the steps of replacing and updating are performed in response to the comparison step and the steps of normalizing, comparing, replacing and updating being performed solely by computer executable instructions being executed by a computer processor in the configuration device and without human intervention;
presenting, by an insulin pump, names for each of the plurality of insulin delivery profiles in the pump configuration file on a display of the insulin pump; and
receiving, by the insulin pump, a selection of one of the insulin delivery profiles; and
delivering insulin, by the insulin pump, to the given patient in accordance with a parameter in the selected insulin delivery profile.

* * * * *